United States Patent
Malik et al.

(10) Patent No.: US 10,889,646 B2
(45) Date of Patent: Jan. 12, 2021

(54) USE OF KIT INHIBITORS TO CONDITION SUBJECTS FOR A HEMATOPOIETIC STEM CELL (HSC) TRANSPLANTATION

(71) Applicant: Children's Hospital Medical Center, Cincinnati, OH (US)

(72) Inventors: Punam Malik, Cincinnati, OH (US); Shanmuganathan Chandrakasan, Cincinnati, OH (US)

(73) Assignee: CHILDREN'S HOSPITAL MEDICAL CENTER, Cincinnati, OH (US)

( * ) Notice: Subject to any disclaimer, the term of this patent is extended or adjusted under 35 U.S.C. 154(b) by 127 days.

(21) Appl. No.: 15/561,126

(22) PCT Filed: Mar. 25, 2016

(86) PCT No.: PCT/US2016/024329
§ 371 (c)(1),
(2) Date: Sep. 25, 2017

(87) PCT Pub. No.: WO2016/154588
PCT Pub. Date: Sep. 29, 2016

(65) Prior Publication Data
US 2018/0127497 A1    May 10, 2018

Related U.S. Application Data

(60) Provisional application No. 62/138,098, filed on Mar. 25, 2015.

(51) Int. Cl.
| | | |
|---|---|---|
| C07K 16/28 | (2006.01) | |
| C07K 14/71 | (2006.01) | |
| A61K 35/28 | (2015.01) | |
| A61K 39/395 | (2006.01) | |
| A61P 7/06 | (2006.01) | |
| A61K 39/00 | (2006.01) | |
| A61K 35/12 | (2015.01) | |

(52) U.S. Cl.
CPC .......... *C07K 16/2803* (2013.01); *A61K 35/28* (2013.01); *A61K 39/3955* (2013.01); *A61P 7/06* (2018.01); *C07K 16/2863* (2013.01); *A61K 2035/124* (2013.01); *A61K 2039/505* (2013.01); *A61K 2039/54* (2013.01); *A61K 2039/55* (2013.01); *C07K 2317/21* (2013.01); *C07K 2317/76* (2013.01)

(58) Field of Classification Search
CPC .............. A61K 2039/505; A61K 38/00; A61K 38/179; A61K 38/177; A61K 39/3955; A61K 38/17; A61K 38/18; C07K 16/18; C07K 2317/76; C07K 14/71; C07K 16/22; C07K 16/2896; C07K 2319/00; C07K 16/2863; C07K 14/70596; C07K 14/475

See application file for complete search history.

(56) References Cited

U.S. PATENT DOCUMENTS

| | | | |
|---|---|---|---|
| 5,489,516 | A | 2/1996 | Broudy et al. |
| 5,545,533 | A | 8/1996 | Bartke et al. |
| 5,808,002 | A | 9/1998 | Buhring |
| 5,919,911 | A | 7/1999 | Broudy et al. |
| 7,144,731 | B2 | 12/2006 | Zsebo et al. |
| 7,915,391 | B2 | 3/2011 | Ng et al. |
| 8,436,150 | B2 | 5/2013 | Ng et al. |
| 2004/0024260 | A1 | 2/2004 | Winkler et al. |
| 2005/0261175 | A1 | 11/2005 | Zsebo et al. |
| 2007/0025395 | A1 | 2/2007 | Cardona et al. |
| 2007/0253951 | A1 | 11/2007 | Ng et al. |
| 2010/2269270 | | 9/2010 | Weismann et al. |
| 2011/0223165 | A1 | 9/2011 | Ng et al. |
| 2013/0288303 | A1 | 10/2013 | Ng et al. |

FOREIGN PATENT DOCUMENTS

WO    WO 2014/018625 A1    1/2014

OTHER PUBLICATIONS

Babaei et al. Receptor tyrosin kinase (c-Kit) inhibitors: a potential therapeutic target in cancer cells. Drug Design Dev Ther 10: 2443-2459, 2016.*
Chandrakasan et al. KIT blockade is sufficient to sustain donor hematopoietic stem cell engraftment in Fanconi Anemia mice. Blood 126(23): 1206; Dec. 3, 2015.*
Chandrakasan et al. KIT blockade is sufficient to sustain donor hematopoietic stem cell engraftment in Fanconi Anemia mice. Blood 129(8): 1048-1052; 2017.*
Chhabra et al. Successful engraftment of hematopoietic stem cell into immunocompetent recipients using only anti-CD117 antibody and CD47 blockade as conditioning. Blood 124(21): 2410; Dec. 6, 2014.*
Finotto et al. Local administration of antisense phosphorothioate oligonucleotides to the c-kit ligand, stem cell factor, suppresses airway inflammation and I-4 production in a murine odel of asthma. J Allergy Clin Immunol 107: 279-286, 2001.*
Gluckman et al. Bone marrow transplantation in Fanconi Anemia. Brit J Haematol 45: 557-564, 1980.*
Leger et al. Hematopoietic stem cell transplantation: a primer for the primary care physician. CMAJ 170(10): 1569-1577, 2004.*

(Continued)

*Primary Examiner* — Bridget E Bunner
(74) *Attorney, Agent, or Firm* — McDermott Will & Emery LLP

(57) ABSTRACT

Provided herein are compositions and methods related to conditioning a subject for a hematopoietic stem cell (HSC) transplantation using an inhibitor of a stem cell growth factor receptor (KIT). The compositions and methods described herein are particularly useful for a subject who is in need of a HSC transplantation and who is hypersensitive to at least one DNA damaging agent, e.g., a subject with fanconi anemia. Compositions and methods related to conditioning a fanconi anemia subject for HSC transplantation using an inhibitor of KIT are also provided herein.

22 Claims, 11 Drawing Sheets

Specification includes a Sequence Listing.

(56) References Cited

OTHER PUBLICATIONS

Logan et al. Anti-CD117 (c-kit) monoclonal antibodies deplete human hematopoietic stem cells and facilitate their replacement in humanized NOD/SCID/IL2Rgamma-/-mice: a non-toxic conditioning regimen for allotransplantation. Blood 120(21): 4099, Nov. 2012.*
Ricotti et al. c-kit is expressed in soft tissue sarcoma of neuroectodermic origin and its ligand prevents apoptosis of neoplastic cells. Blood 91(7): 2397-2405, 1998.*
Turner et al. Identification and characterization of a soluble c-kit receptor produced by human hematopoietic cell lines. Blood 85(8): 2052-2058, 1995.*
Wu et al. Silencing of c-kit with small interference RNA attenuates inflammation in murine model of allergic asthma. Int J Mol Med 30: 63-68, 2012.*
Fewkes et al. Pharmacologic modulation of niche accessibility via tyrosine kinase inhibition enhances marrow and thymic engraftment after hematopoietic stem cell transplantation. Blood 115(20): 4120-4129, 2010.*
Dufour et al. Fanconi anemia: new strategies. Bone Marrow Transplant 41: S90-S95, 2008.*
Hays et al. (Fanconi Anemia: Guidelines for Diagnosis and Management, fourth edition, Eugene, OR, 2014, pp. 219-243.*
Brummelkamp et al., A system for stable expression of short interfering RNAs in mammalian cells. Science. Apr. 19, 2002;296(5567):550-3. Epub Mar. 21, 2002.
Czechowicz et al., Efficient transplantation via antibody-based clearance of hematopoietic stem cell niches. Science. Nov. 23, 2007;318(5854):1296-9.
Hannon, RNA interference. Nature. Jul. 11, 2002;418(6894):244-51.
Sui et al., A DNA vector-based RNAi technology to suppress gene expression in mammalian cells. Proc Natl Acad Sci U S A. Apr. 16, 2002;99(8):5515-20.
Xue et al., Antibody targeting KIT as pretransplantation conditioning in immunocompetent mice. Blood. Dec. 9, 2010;116(24):5419-22. doi: 10.1182/blood-2010-07-295949. Epub Sep. 2, 2010.

* cited by examiner

| Major Differentially Expressed Pathway | p value |
|---|---|
| INFLAMMATION | |
| Abnormal innate immunity ↑ | 2.27E-17 |
| Interferon Signaling ↑ | 1.92E-04 |
| Interferon gamma signaling ↑ | 3.73E-04 |
| HSC STRESS | |
| HIF-1-alpha transcription factor network ↑ | 5.95E-08 |
| DNA damage response ↑ | 1.21E-05 |
| ATM Signaling Pathway ↑ | 2.92E-04 |
| p53 Signaling Pathway ↑ | 5.26E-04 |
| HSC SURVIVAL | |
| Wnt Signaling Pathway ↓ | 2.41E-04 | a)

b)

(a)

40mg/kg ip

Days 0    2    5    7

Congenic BM HCT
With 20e6 45.1 BM cells (b)

(c)

USE OF KIT INHIBITORS TO CONDITION SUBJECTS FOR A HEMATOPOIETIC STEM CELL (HSC) TRANSPLANTATION

CROSS-REFERENCE TO RELATED APPLICATIONS

This application is a national stage filing under 35 U.S.C. § 371 of PCT International Application No. PCT/US2016/024329, filed Mar. 25, 2016, which claims the benefit under 35 U.S.C. § 119(e) of U.S. provisional application No. 62/138,098 filed Mar. 25, 2015, the contents of each of which are incorporated by reference herein in their entirety.

BACKGROUND

Fanconi anemia (FA) is characterized by progressive bone marrow failure (BMF), hypersensitivity to DNA-damaging agents and a high incidence of cancer. Currently, hematopoietic stem cell transplant (HSCT) is the only therapeutic option for the BMF. Due to the underlying DNA repair defect, FA patients, however, have inherent hypersensitivity to DNA cross-linking/alkylating agents such as cyclophosphamide, busulfan and irradiation. Gluckman et al. *British journal of haematology.* 1980; 45(4):557-64. Despite reduced-intensity alkylator conditioning, there is still an increased risk of infertility, cataracts, endocrinopathies, and a high incidence of second malignancy in FA HSCT recipients. Socie et al. *British journal of haematology.* 1998; 103(1):249-55. To overcome these adverse effects, alternative experimental approaches exploiting the inherent hematopoietic stem cell (HSC) defect in FA have been attempted without significant success. Li et al. *Blood.* 2004; 104(4): 1204-9.

Unlike humans, murine models of FA do not develop overt BMF. Instead, they have subtle defects in hematopoietic stem/progenitor cell (HSPC) number and function. Parmar et al. *Stem cells.* 2010; 28(7):1186-95; and Carreau et al. *Experimental hematology.* 1999; 27(11):1667-74. A more apparent defect is evident under experimentally-induced hematopoietic stress. Haneline et al. *Blood.* 1998; 91(11):4092-8; and Cheng et al. *Human molecular genetics.* 2000; 9(12):1805-11. Cytokinesis failure (Vinciguerra et al. *The Journal of clinical investigation.* 2010; 120(11):3834-42), increased p53 activation leading to p21 mediated HSC senescence (Ceccaldi et al. *Cell stem cell.* 2012; 11(1):36-49), inflammatory cytokine driven apoptosis (Haneline et al. *Blood.* 1998; 91(11):4092-8), and exhaustion of HSC from increased cycling and cycling-induced accumulation of DNA damage are some of the mechanisms proposed for BMF in FA. Walter et al. *Nature.* 2015; 520(7548):549-52. Based on hypersensitivity of FA HSPCs to pro-inflammatory cytokines such as IFN-γ (Haneline et al. *Blood.* 1998; 91(11):4092), continuous exposure of the host HSPCs to IFN-γ has been shown to facilitate donor HSC engraftment in different FA mouse models. Li et al. *Blood.* 2004; 104 (4):1204-9; and Si et al. *Blood.* 2006; 108(13):4283-7. However, its translation has been limited, likely due to the known TNF-α induction by IFN-γ, and findings of leukemic clonal evolution following TNF-α exposure in F A. Li et al. *The Journal of clinical investigation.* 2007; 117(11):3283-95; and Vila-del Sol et al. *J Immunol.* 2008; 181(7):4461-70. Hence, there is a need for alternative non-alkylator-based HSC-targeted conditioning regimens with minimal toxicity, which can be, for example, beneficial for FA patients.

SUMMARY

The present disclosure is, in part, based on the unexpected discovery that blocking the binding of stem cell factor (SCF) to its cognate receptor, KIT, successfully induced apoptosis in hematopoietic stem cells and/or progenitor cells (HSPCs), that are defective in DNA repair, thereby facilitating donor HSPC engraftment in fanconi anemia (FA) mice.

Accordingly, one aspect of the present disclosure features a method for conditioning a subject for an HSC transplantation by administering an effective amount of an KIT inhibitor to a subject who is in need of an HSC transplantation and is hypersensitive to at least one DNA damaging agent (e.g., an alkylating agent such as busulfan). For example, the subject can be defective in DNA repair.

In another aspect, the present disclosure provides a method of conditioning a subject for an HSC transplantation, the method comprising administering to a subject who is in need of a HSC transplantation an effective amount of a KIT inhibitor. The subject may be free of irradiation treatment. In some examples, the subject is also hypersensitive to at least one DNA damaging agent.

Any of the methods described herein may further comprise transplanting a first population of HSCs to the subject after administration of the KIT inhibitor, and optionally transplanting a second population of HSCs to the subject after the transplantation of the first HSC population.

Further, the present disclosure provides a method of treating fanconi anemia in a subject in need of the treatment. The method comprises: (a) administering an effective amount of an inhibitor of a stem cell growth factor receptor (KIT) to a subject who has fanconi anemia, (b) transplanting a first population of HSCs to the subject after (a), and optionally (c) transplanting a second population of HSCs to the subject after (b).

In any of the methods described herein, the amount of the inhibitor KIT can be effective to induce apoptosis of endogenous HSCs and HSPCs, and/or promote engraftment of the HSCs transplanted to the subject.

In some embodiment, the first population of HSCs can be transplanted to the subject after the inhibitor of KIT is substantially cleared from serum of the subject. In some examples, the first population of HSCs can be transplanted to the subject at least 24 hours after the administration of the inhibitor of KIT. In other examples, the first population of HSCs can be transplanted to the subject at least 3 days (e.g., at least 7 days) after the administration of the inhibitor of KIT.

In some embodiments, the subject to be treated by any of the methods described herein may be free of any further conditioning treatment, e.g., irradiation treatment or administration of a DNA damaging agent, before the transplantation of HSCs.

In any methods described herein, the first population of HSCs, the second population of HSCs, or both for transplantation can be derived from bone marrow, peripheral blood cells, and/or umbilical cord blood of a suitable source (e.g., human). The HSCs can be allogeneic HSCs or autologous HSCs. In some examples, the HSCs can be cultured ex vivo prior to transplantation to a subject.

In any aspects described herein, the inhibitor of KIT can be a protein, a nucleic acid, a small molecule, or a combination thereof. In some examples, the inhibitor of KIT can be a KIT blocking antibody (e.g., an antibody that binds KIT and blocks SCF/KIT signaling). The antibody can be a human antibody.

In any of the methods described herein, the subject can be a human subject. In some embodiments, the subject is a human patient having fanconi anemia.

Also within the scope of the present disclosure are (i) a pharmaceutical composition for use in promoting engraftment of donor HSCs in a subject who is in need for a HSC transplantation or conditioning a subject for a HSC transplantation, the composition comprising any of the KIT inhibitors described herein and a pharmaceutically acceptable carrier; and (ii) use of an KIT inhibitor in manufacturing a medicament for use in promoting engraftment of donor HSCs in a subject who is in need for a HSC transplantation or conditioning a subject for a HSC transplantation or for treating FA. The subject can be hypersensitive to at least one DNA damaging agent (e.g., a subject who has fanconi anemia).

The details of one or more embodiments of the disclosure are set forth in the description below. Other features or advantages of the present disclosure will be apparent from the following drawings and detailed description of several embodiments, and also from the appended claims.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein.

DETAILED DESCRIPTION OF THE INVENTION

Figure 1:
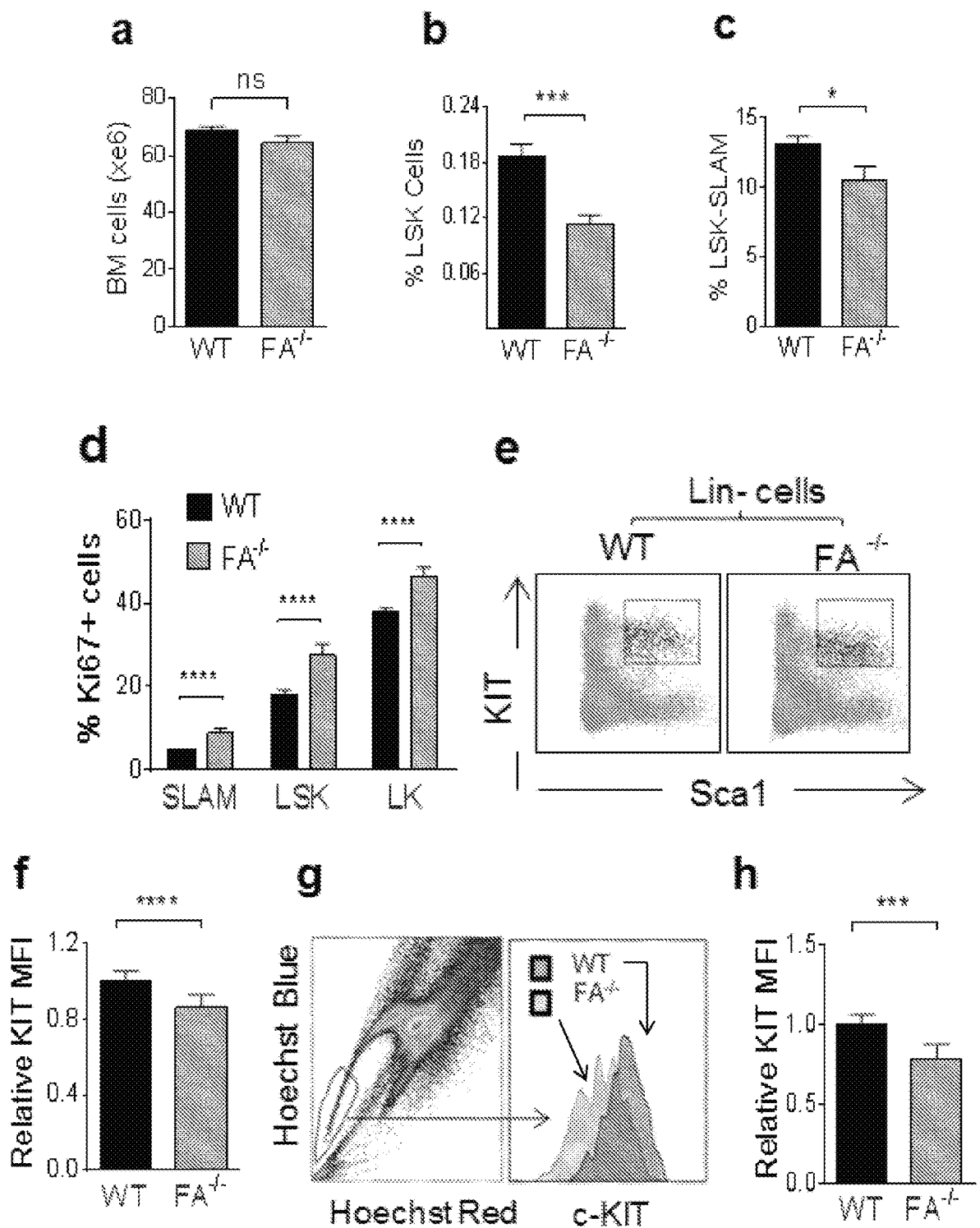
FIG. 1 includes diagrams showing that FANCA mice HSPC were reduced in number, actively proliferated with increased KIT signaling and displayed an expression profile prone to apoptosis and senescence. (Panels a-c) Whole bone marrow, LSK and LSK SLAM cells from two femurs (WT n=16, FA$^{-/-}$, n=18). (Panel d) Percentage Ki67+ (cycling) HSPC from WT and FA bone marrow (WT n=5, FA$^{-/-}$, n=5). (Panels e-h) KIT expression on LSK cells (WT n=17, FA$^{-/-}$, n=19) and Lin-Side Population (SP) cells (WT n=7, FA$^{-/-}$, n=5). (Panel i) Stromal SCF mRNA expression (WT n=6, FA$^{-/-}$, n=4). (Panels j-k) Differentially expressed genes in WT and FA LSK cells (WT n=3, FA$^{-/-}$, n=3). (Panels l and m) Percentage of Annexin-V positive cells following 48 hours of culture in medium containing SCF and TPO C12 FDG staining of LSK cells (WT n=3, FA$^{-/-}$, n=3) and (Panels n and o) C12 FDG staining of LSK cells (WT n=3, FA$^{-/-}$, n=3) **P<0.0001,*P<0.001,**P<0.01,*P<0.05 (Student t test).
Figure 1:
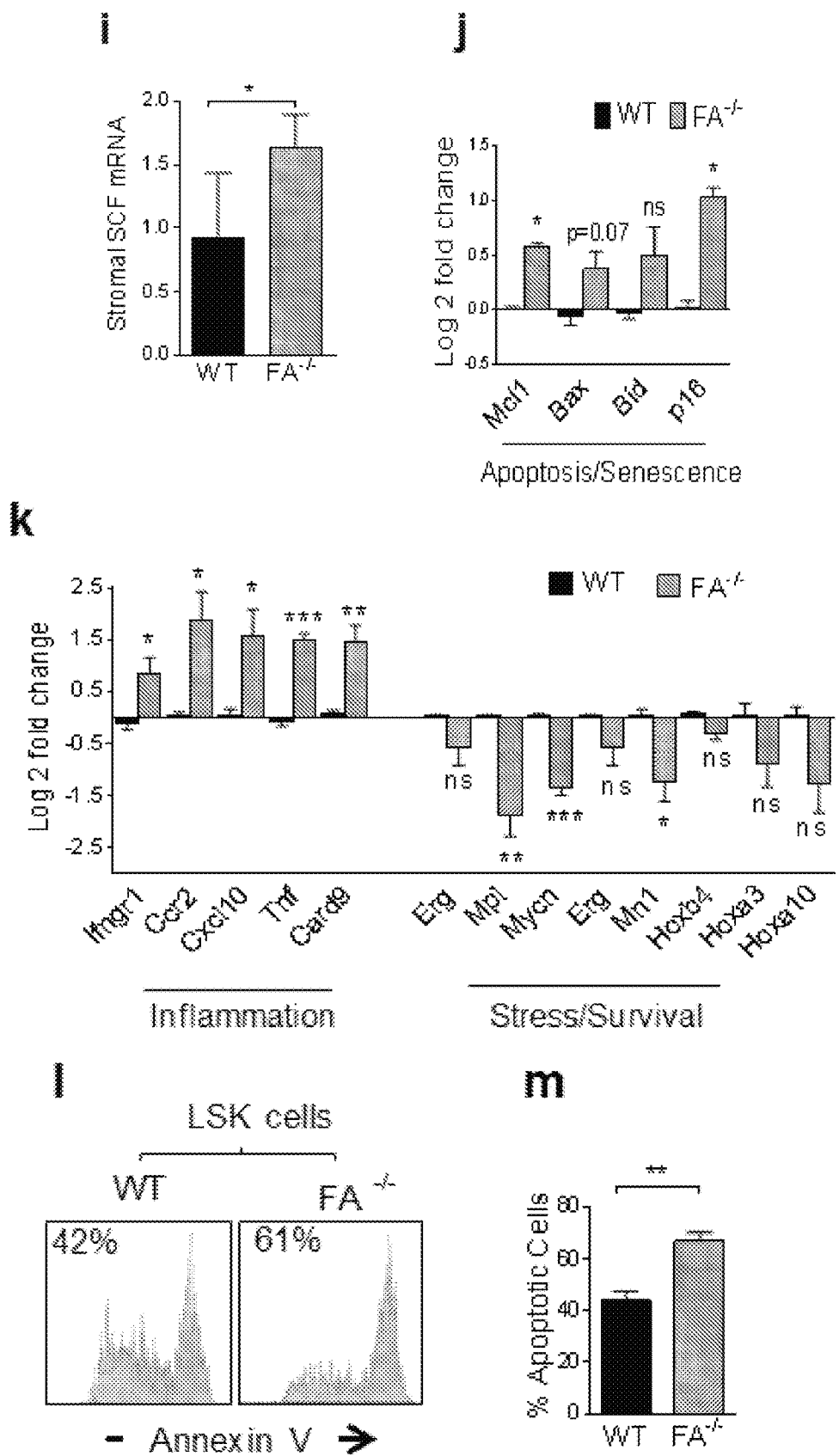
Figure 1:
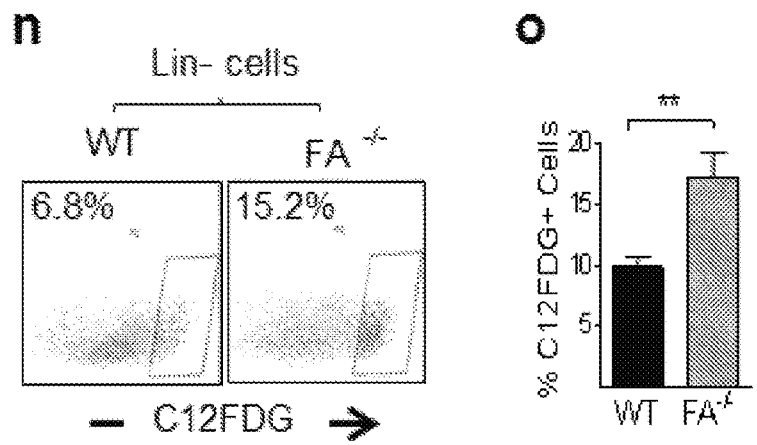

Currently, patients who are in need of a hematopoietic stem cell (HSC) transplantation generally receive a potent alkylating agent, e.g., busulfan, and/or irradiation, prior to receiving a HSC transplantation to ensure adequate donor HSC engraftment. However, patients who are hypersensitive to DNA damaging agents (e.g., alkylating agents and/or irradiation) typically tolerate such agents poorly, thus suffering from various adverse effects, e.g., increased risk of infertility, cataracts, and/or endocrinopathies, as well as long-germ risk of secondary malignancy such as increased secondary squamous cell carcinoma. Such patients include those who are defective in DNA repair and thus are unable to repair DNA damages caused by an alkylating agent. Accordingly, there is a need to develop non-genotoxic methods and compositions for conditioning subjects who are in need of a HSC transplantation.

The present disclosure is, in part, based on the unexpected discovery that hematopoietic stem cells and/or progenitor cells (HSPCs) that are defective in DNA repair are predisposed to apoptosis mediated by inhibition of the signaling pathway triggered by the interaction between stem cell factor (SCF) and its cognate receptor, KIT. For example, such HSPCs showed increased KIT signaling, increased baseline activation of apoptosis, inflammatory, and/or senescence pathways, and/or reduced baseline activation of stress handling and/or survival pathways. In particular, it was discovered that subjects with fanconi anemia (FA) contain these HSPCs that are susceptible to KIT blockade-mediated apoptosis. Further, it was discovered that blocking the binding between SCF and KIT (e.g., via an anti-KIT antibody) enhanced apoptosis of endogenous or host hematopoietic stem/progenitor cells (HSPCs) in FA mice and/or facilitated engraftment of donor HSCs transplanted into the FA mice.

Accordingly, described herein are methods and compositions for conditioning a subject for an HSC transplantation using an KIT inhibitor, which mediates apoptosis of the subject's endogenous HSPCs (i.e., host HSPCs). Such a subject can be defective in DNA repair (e.g., a human patient having fanconi anemia). The methods and compositions described herein promote engraftment of donor HSCs in the subject after HSC transplantation.

In some aspects, the disclosure relates to methods of conditioning a subject for a hematopoietic stem cell (HSC) transplantation using an KIT inhibitor, which can improve the efficacy of the HSC transplantation in the subject. For example, the KIT inhibitor can enhance engraftment of donor HSCs in the subject after transplantation.

I. Inhibitors of a Stem Cell Factor Receptor (KIT) or KIT Inhibitors

Stem cell factor receptor (KIT) is a cytokine receptor expressed on the surface of hematopoietic stem cells and/or progenitor cells as well as other cell types. It is also known as mast/stem cell growth factor receptor (SCFR), c-KIT, tyrosine protein kinase Kit, or CD117. KIT is a receptor tyrosine kinase type III, which binds to stem cell factor (SCF).

As used herein, the term "KIT" generally refers to a KIT polypeptide or KIT polynucleotide having the same or similar bioactivity of a wild-type KIT.

In some embodiments, the term "KIT" refers to a KIT polypeptide having an amino acid sequence that is at least 70% or more (including at least 75%, at least 80%, at least 85%, at least 90%, at least 95%, at least 97%, at least 99%, or 100%) identical to that of a wild-type KIT, and is capable of binding SCF and triggering the SCF/KIT signaling pathway.

The "percent identity" of two amino acid sequences is determined using the algorithm of Karlin and Altschul *Proc. Natl. Acad. Sci. USA* 87:2264-68, 1990, modified as in Karlin and Altschul *Proc. Natl. Acad. Sci. USA* 90:5873-77, 1993. Such an algorithm is incorporated into the NBLAST and XBLAST programs (version 2.0) of Altschul, et al. *J. Mol. Biol.* 215:403-10, 1990. BLAST protein searches can be performed with the XBLAST program, score=50, wordlength=3 to obtain amino acid sequences homologous to the protein molecules of the invention. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NBLAST) can be used.

Wild-type KIT sequences of various species are available on the world wide web from the NCBI, including human, mouse, rat, dog, cat, monkey, and chimpanzee. For example, the nucleotide sequence encoding human KIT is available at NCBI under Accession No. NM_000222 or NM_001093772 and its corresponding amino acid sequence is under Accession No. NP_000213 and NP_001087241, respectively. The protein sequences of human KIT are provided below.

```
>gi|4557695|ref|NP_000213.1| mast/stem cell growth
factor receptor Kit isoform 1 precursor
[Homo sapiens]
                                         (SEQ ID NO: 1)
MRGARGAWDFLCVLLLLLRVQTGSSQPSVSPGEPSPPSIHPGKSDLIVRV

GDEIRLLCTDPGFVKWTFEILDETNENKQNEWITEKAEATNTGKYTCTNK

HGLSNSIYVFVRDPAKLFLVDRSLYGKEDNDTLVRCPLTDPEVTNYSLKG

CQGKPLPKDLRFIPDPKAGIMIKSVKRAYHRLCLHCSVDQEGKSVLSEKF

ILKVRPAFKAVPVVSVSKASYLLREGEEFTVTCTIKDVSSSVYSTWKREN

SQTKLQEKYNSWHHGDFNYERQATLTISSARVNDSGVFMCYANNTFGSAN

VTTTLEVVDKGFINIFPMINTTVFVNDGENVDLIVEYEAFPKPEHQQWIY

MNRTFTDKWEDYPKSENESNIRYVSELHLTRLKGTEGGTYTFLVSNSDVN

AAIAFNVYVNTKPEILTYDRLVNGMLQCVAAGFPEPTIDWYFCPGTEQRC

SASVLPVDVQTLNSSGPPFGKLVVQSSIDSSAFKHNGTVECKAYNDVGKT

SAYFNFAFKGNNKEQIHPHTLFTPLLIGFVIVAGMMCIIVMILTYKYLQK

PMYEVQWKVVEEINGNNYVYIDPTQLPYDHKWEFPRNRLSFGKTLGAGAF

GKVVEATAYGLIKSDAAMTVAVKMLKPSAHLTEREALMSELKVLSYLGNH

MNIVNLLGACTIGGPTLVITEYCCYGDLLNFLRRKRDSFICSKQEDHAEA

ALYKNLLHSKESSCSDSTNEYMDMKPGVSYVVPTKADKRRSVRIGSYIER

DVTPAIMEDDELALDLEDLLSFSYQVAKGMAFLASKNCIHRDLAARNILL

THGRITKICDFGLARDIKNDSNYVVKGNARLPVKWMAPESIFNCVYTFES

DVWSYGIFLWELFSLGSSPYPGMPVDSKFYKMIKEGFRMLSPEHAPAEMY

DIMKTCWDADPLKRPTFKQIVQLIEKQISESTNHIYSNLANCSPNRQKPV

VDHSVRINSVGSTASSSQPLLVHDDV

>gi|148005039|ref|NP_001087241.1| mast/stem cell
growth factor receptor Kit isoform 2 precursor
[Homo sapiens]
                                         (SEQ ID NO: 2)
MRGARGAWDFLCVLLLLLRVQTGSSQPSVSPGEPSPPSIHPGKSDLIVRV

GDEIRLLCTDPGFVKWTFEILDETNENKQNEWITEKAEATNTGKYTCTNK

HGLSNSIYVFVRDPAKLFLVDRSLYGKEDNDTLVRCPLTDPEVTNYSLKG

CQGKPLPKDLRFIPDPKAGIMIKSVKRAYHRLCLHCSVDQEGKSVLSEKF

ILKVRPAFKAVPVVSVSKASYLLREGEEFTVTCTIKDVSSSVYSTWKREN
```

-continued

```
SQTKLQEKYNSWHHGDFNYERQATLTISSARVNDSGVFMCYANNTFGSAN

VTTTLEVVDKGFINIFPMINTTVFVNDGENVDLIVEYEAFPKPEHQQWIY

MNRTFTDKWEDYPKSENESNIRYVSELHLTRLKGTEGGTYTFLVSNSDVN

AAIAFNVYVNTKPEILTYDRLVNGMLQCVAAGFPEPTIDWYFCPGTEQRC

SASVLPVDVQTLNSSGPPFGKLVVQSSIDSSAFKHNGTVECKAYNDVGKT

SAYFNFAFKEQIHPHTLFTPLLIGFVIVAGMMCIIVMILTYKYLQKPMYE

VQWKVVEEINGNNYVYIDPTQLPYDHKWEFPRNRLSFGKTLGAGAFGKVV

EATAYGLIKSDAAMTVAVKMLKPSAHLTEREALMSELKVLSYLGNHMNIV

NLLGACTIGGPTLVITEYCCYGDLLNFLRRKRDSFICSKQEDHAEAALYK

NLLHSKESSCSDSTNEYMDMKPGVSYVVPTKADKRRSVRIGSYIERDVTP

AIMEDDELALDLEDLLSFSYQVAKGMAFLASKNCIHRDLAARNILLTHGR

ITKICDFGLARDIKNDSNYVVKGNARLPVKWMAPESIFNCVYTFESDVWS

YGIFLWELFSLGSSPYPGMPVDSKFYKMIKEGFRMLSPEHAPAEMYDIMK

TCWDADPLKRPTFKQIVQLIEKQISESTNHIYSNLANCSPNRQKPVVDHS

VRINSVGSTASSSQPLLVHDDV
```

As used herein, the term "inhibitor" is used in the broadest sense, and includes any molecule that partially or fully blocks, inhibits, or neutralizes a biological activity of a native polypeptide disclosed herein (e.g., KIT). Suitable inhibitor molecules specifically include antagonist antibodies or antibody fragments, fragments or amino acid sequence variants of native polypeptides, peptides, antisense oligonucleotides, small organic molecules, recombinant proteins or peptides, etc. Methods for identifying inhibitors of a polypeptide can comprise contacting a polypeptide with a candidate KIT inhibitor molecule and measuring a detectable change in one or more biological activities normally associated with the polypeptide.

A KIT inhibitor or an inhibitor of a SCF receptor KIT is an agent that interferes with the KIT signaling in a cell, for example, either by decreasing transcription or translation of KIT-encoding nucleic acid, or by inhibiting or blocking KIT polypeptide activity, or both. Examples of KIT inhibitors include, but are not limited to, antisense polynucleotides, interfering RNAs, catalytic RNAs, RNA-DNA chimeras, KIT-specific aptamers, anti-KIT antibodies, KIT-binding fragments of anti-KIT antibodies, KIT-binding small molecules, KIT-binding peptides, and other polypeptides that specifically bind KIT (including, but not limited to, KIT-binding fragments of one or more KIT ligands, optionally fused to one or more additional domains), such that the interaction between the KIT inhibitor and KIT results in a reduction or cessation of KIT activity or expression. It will be understood by one of ordinary skill in the art that in some instances, a KIT inhibitor can antagonize or neutralize one KIT activity without affecting another KIT activity. For example, a desirable KIT inhibitor for use in certain of the methods herein is a KIT inhibitor that disrupts binding interaction between KIT and SCF, e.g., without affecting or minimally affecting any of the other KIT interactions, if any.

In some embodiments, a KIT inhibitor is an agent that directly or indirectly inhibits or reduces the KIT-mediated apoptosis of endogenous or host HSPCs in a subject. Accordingly, a KIT inhibitor can target the KIT or its corresponding ligand (e.g., SCF), or any of KIT's upstream molecules. Examples of KIT inhibitors include, without limitations, anti-KIT molecules, SCF inhibitors, and a combination thereof. A KIT inhibitor can be a protein, a peptide, a peptidomimetic, an aptamer, a nucleic acid, an antibody, a small molecule, or any combinations thereof.

In some embodiments, a KIT inhibitor can be a fragment or variant of KIT itself, e.g., a fragment that binds a KIT ligand (e.g., SCF) but does not transmit KIT/SCF signaling. A KIT inhibitor of this type can be a dominant negative inhibitor.

A KIT inhibitor can be an agent (e.g., an antibody or a small molecule) that interferes with the interaction between KIT and a ligand thereof, SCF. The KIT inhibitor can also be an agent (e.g., a inhibitory polynucleotide or oligonucleotide such as interfering RNA or antisense oligonucleotide) that suppresses KIT transcription and/or translation, thereby reducing the mRNA/protein level of this receptor. The KIT inhibitor as described herein may reduce the KIT signaling in cells by at least 20% or more, e.g., 30%, 40%, 50%, 60%, 70%, 80%, 90%, 95% or above. The inhibitory activity of such an inhibitor against KIT can be determined by conventional methods, e.g., measuring viability and survival of c-Kit dependent cells such as human megakaryoblastic cell line UT-7 as disclosed in U.S. Pat. No. 7,915,391, the relevant disclosure of which is incorporated herein by reference for its intended purpose.

In some embodiments, the KIT inhibitor is an antibody that specifically binds to KIT and neutralizes its binding activity or affinity to SCF. As used herein, the term "antibody" as includes but is not limited to polyclonal, monoclonal, humanized, chimeric, Fab fragments, Fv fragments, F(ab') fragments and F(ab')2 fragments, as well as single chain antibodies (scFv), fusion proteins and other synthetic proteins which comprise the antigen-binding site of the antibody.

Antibodies can be made by the skilled person using methods and commercially available services and kits known in the art. Methods of preparation of monoclonal antibodies are well known in the art and include hybridoma technology and phage display technology. Further antibodies suitable for use in the present disclosure are described, for example, in the following publications: Antibodies A Laboratory Manual, Second edition. Edward A. Greenfield. Cold Spring Harbor Laboratory Press (Sep. 30, 2013); Making and Using Antibodies: A Practical Handbook, Second Edition. Eds. Gary C. Howard and Matthew R. Kaser. CRC Press (Jul. 29, 2013); Antibody Engineering: Methods and Protocols, Second Edition (Methods in Molecular Biology). Patrick Chames. Humana Press (Aug. 21, 2012); Monoclonal Antibodies: Methods and Protocols (Methods in Molecular Biology). Eds. Vincent Ossipow and Nicolas Fischer. Humana Press (Feb. 12, 2014); and Human Monoclonal Antibodies: Methods and Protocols (Methods in Molecular Biology). Michael Steinitz. Humana Press (Sep. 30, 2013)).

Antibodies may be produced by standard techniques, for example by immunization with the appropriate polypeptide or portion(s) thereof, or by using a phage display library. If polyclonal antibodies are desired, a selected mammal (e.g., mouse, rabbit, goat, horse, etc) is immunized with an immunogenic polypeptide bearing a desired epitope(s), optionally haptenized to another polypeptide. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Serum from the immunized animal is collected and treated according to known procedures. If serum containing polyclonal antibodies to the desired epitope contains antibodies to other antigens, the polyclonal antibodies can be purified by immunoaffinity chromatography or any other method known in the art. Techniques for producing and processing polyclonal antisera are well known in the art.

An antibody specifically binds to KIT if the antibody binds KIT with a greater affinity than for an irrelevant polypeptide. In some embodiments, the antibody binds KIT with at least 5, or at least 10 or at least 50 times greater affinity than for the irrelevant polypeptide. In some embodiments, the antibody binds KIT with at least 100, or at least 1,000, or at least 10,000 times greater affinity than for the irrelevant polypeptide. Such binding may be determined by methods well known in the art, such surface plasmon resonance such as a Biacore® system. In some embodiments, the antibody has an affinity (as measured by a dissociation constant, $K_D$) for KIT of at least $10^{-7}$ M, $10^{-8}$ M, 10 M, $10^{-10}$ M, or $10^{-11}$ M.

Anti-KIT antibodies are commercially available. See, e.g., products from Abcam, including but not limited to Anti-c-Kit antibody (ab5506 or ab5505), Anti-c-Kit antibody [YR145] (ab32363), Anti-c-Kit antibody [104D2] (ab111033); products from Cell Signaling Technology, including but not limited to c-Kit antibody (#3392); and products from R&D Systems including but not limited to human CD117/c-kit antibodies (#AF1356, AF332, MAB 332, and AF3267).

Other antibodies that bind to KIT and inhibit or reduce its binding to SCF, as well as polynucleotides encoding anti-KIT antibodies are described in U.S. Pat. Nos. 5,808,002; 5,545,533; 5,919,911; and 5,489,516; 7,915,391 and 8,436,150; in U.S. Patent Publication Nos. US2004/024260; US2007/0253951; US2011/0223165; and US2013/0288303; and in the International Patent Publication No. WO2014/018625, the relevant disclosures of which are incorporated by reference herein for the intended purpose.

In some examples, the anti-KIT antibodies described herein are full human antibodies. Full human antibodies can be obtained by using commercially available animals (e.g., mice) that have been engineered to express specific human immunoglobulin proteins. Transgenic animals that are designed to produce a more desirable (e.g., fully human antibodies) or more robust immune response may also be used for generation of humanized or human antibodies. Examples of such technology are XenoMouse™ from Amgen, Inc. (Fremont, Calif.) and HuMAb-Mouse™ and TC Mouse™ from Medarex, Inc. (Princeton, N.J.). In another alternative, antibodies may be made recombinantly by phage display or yeast technology. See, for example, U.S. Pat. Nos. 5,565,332; 5,580,717; 5,733,743; and 6,265,150; and Winter et al., (1994) Annu. Rev. Immunol. 12:433-455, and . Alternatively, the phage display technology (McCafferty et al., (1990) Nature 348:552-553) can be used to produce human antibodies and antibody fragments in vitro, from immunoglobulin variable (V) domain gene repertoires from unimmunized donors.

In other examples, the anti-KIT antibodies are humanized antibodies. Humanized antibodies refer to antibodies derived from non-human (e.g. murine) antibodies that are specific chimeric immunoglobulins, immunoglobulin chains, or antigen-binding fragments thereof that contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, six) which are altered with respect to the original antibody, which are also termed one or more CDRs "derived from" one or more CDRs from the original antibody. Humanized antibodies may also involve affinity maturation. Methods for constructing humanized antibodies are also well known in the art. See, e.g., Queen et al., Proc. Natl. Acad. Sci. USA, 86:10029-10033 (1989).

In some embodiments, an inhibitor of KIT can be a humanized c-KIT antibody designated as humanized SR-1 in the U.S. Pat. No. 7,915,391 or in U.S. Patent Application No. US2007/025395, the relevant disclosures of which are incorporated herein by reference for the intended purpose.

In another example, the antibody described herein is a chimeric antibody, which can include a heavy constant region and a light constant region from a human antibody. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or the constant region.

In some embodiments, the KIT inhibitor is an interfering RNA such as a small interfering RNA (siRNA) short hairpin RNA (shRNA). In some embodiments, the KIT inhibitor is a small interfering RNA (siRNA) that binds to a KIT mRNA and blocks its translation or degrades the mRNA via RNA interference. Exemplary small interfering RNAs are described by Hannon et al. Nature, 418 (6894): 244-51 (2002); Brummelkamp et al., Science 21 , 21 (2002); and Sui et al., Proc. Natl Acad. Sci. USA 99, 5515-5520 (2002). RNA interference (RNAi) is the process of sequence-specific post-transcriptional gene silencing in animals initiated by double-stranded (dsRNA) that is homologous in sequence to the silenced gene. siRNAs are generally RNA duplexes with each strand being 20-25 (such as 19-21) base pairs in length. In some embodiments, the KIT inhibitor is a short hairpin RNA (shRNA) that is complementary to a KIT nucleic acid (e.g., a KIT mRNA). An shRNA typically contains of a stem of 19-29 base pairs, a loop of at least 4 nucleotides (nt), and optionally a dinucleotide overhang at the 3' end. Expression of shRNA in a subject can be obtained by delivery of a vector (e.g., a plasmid or viral or bacterial vectors) encoding the shRNA. siRNAs and shRNAs may be designed using any method known in the art or commercially available (see, e.g., products available from Dharmacon and Life Technologies). An siRNA may also comprise one or more chemical modifications, such as a base modification and/or a bond modification to at least improve its stability and binding affinity to the target mRNA.

In some embodiments, the KIT inhibitor is an antisense oligonucleotide that is complementary to a KIT nucleic acid (e.g., a KIT mRNA). Antisense oligonucleotides are generally single-stranded nucleic acids (either a DNA, RNA, or hybrid RNA-DNA molecule), which are complementary to a target nucleic acid sequence, such as a portion of a KIT mRNA. By binding to the target sequence, an RNA-RNA, a DNA-DNA, or RNA-DNA duplex is formed, thereby inhibiting the function or level of the target nucleic acid, such as by blocking the transcription, processing, poly(A) addition, replication, translation, or promoting inhibitory mechanisms of the cells, such as promoting mRNA degradation. In some embodiments, an antisense oligonucleotide is 10 to 40, 12 to 35, or 15 to 35 bases in length, or any integer in between. An antisense oligonucleotide can comprise one or more modified bases, such as 2-Aminopurine, 2,6-Diaminopurine (2-Amino-dA), 5-Bromo dU, 5-Methyl dC, deoxyInosine, Locked Nucleic Acid (LNA), 5-Nitroindole, 2'-O-Methyl bases, Hydroxmethyl dC, 2' Fluoro bases. An antisense oligonucleotide can comprise one or more modified bonds, such as a phosphorothioate bond.

In some embodiments, the KIT inhibitor is a ribozyme that is complementary to a KIT nucleic acid (e.g., a KIT mRNA) and cleaves the KIT nucleic acid. Ribozymes are RNA or RNA-protein complexes that cleave nucleic acids in a site-specific fashion. Ribozymes have specific catalytic domains that possess endonuclease activity. The ribozymes of the present disclosure may be synthetic ribozymes, such as those described in U.S. Pat. No. 5,254,678. These synthetic ribozymes have separate hybridizing regions and catalytic regions; therefore, the hybridizing regions can be designed to recognize a target sequence, such as a KIT sequence as described herein.

siRNAs, shRNAs, ribozymes, and antisense oligonucleotides as described herein may be complementary to a KIT nucleic acid (e.g., a KIT mRNA), or a portion thereof. It is to be understood that complementarity includes 100% complementarity but does not necessarily exclude mismatches at one or more locations, resulting in, e.g., at least 80%, at least 90%, at least 95%, at least 98%, or at least 99% complementarity.

When applicable, the KIT inhibitor can be expressed from a vector, which may be used for delivering the KIT inhibitor into a subject who needs a HSC transplantation. A "vector", as used herein is any vehicle capable of facilitating the transfer of a KIT inhibitor (e.g., a shRNA, siRNA, ribozyme, antisense oligonucleotide, protein, peptide, or antibody) to a cell in the subject, such as a cell expressing receptor KIT. In general, vectors include, but are not limited to, plasmids, phagemids, viruses, and other vehicles derived from viral or bacterial sources that have been manipulated by the insertion or incorporation of a sequence encoding a KIT inhibitor. Viral vectors include, but are not limited to nucleic acid sequences from the following viruses: retrovirus; lentivirus; adenovirus; adeno-associated virus; SV40-type viruses; polyoma viruses; Epstein-Barr viruses; papilloma viruses; herpes virus; vaccinia virus; polio virus. One can readily employ other vectors not named but known to the art.

Viral vectors may be based on non-cytopathic eukaryotic viruses in which nonessential genes have been replaced with a sequence encoding a KIT inhibitor. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are known in the art.

Other viral vectors include adeno-viruses and adeno-associated viruses, which are double-stranded DNA viruses that have also been approved for human use in gene therapy. The adeno-associated virus can be engineered to be replication deficient and is capable of infecting a wide range of cell types and species.

Other vectors include plasmid vectors. Plasmid vectors have been extensively described in the art and are well known to those of skill in the art. See, e.g., Sambrook et al. Molecular Cloning: A Laboratory Manual. Cold Spring Harbor Laboratory Press; 4th edition (Jun. 15, 2012). Exemplary plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA, such as a sequence encoding a KIT inhibitor.

In some embodiments, KIT inhibitor nucleic acid sequence is under the control of a heterologous regulatory region, e.g., a heterologous promoter. The promoter can be, e.g., a ubiquitous promoter such as a CMV promoter, ActB promoter, or Ubiquitin B promoter. The promoter can also be a tissue-specific promoter or synthetic promoter. Promoters are well known in the art and commercially available (see, e.g., products available from InvivoGen).

In some embodiments, the KIT inhibitor is a non-antibody peptide or protein. The peptide or protein may comprise an amino acid sequence that interferes with the KIT signaling, such as by competing with a natural ligand for KIT, e.g., competing with SCF. Proteins and peptides may be designed using any method known in the art, e.g., by screening libraries of proteins or peptides for binding to KIT or inhibition of KIT binding to a ligand, such as KIT.

In some embodiments, the KIT inhibitor is a small molecule, such as a small organic molecule, which typically has a molecular weight less than 5,000 kDa. Suitable small molecules include those that bind to KIT, or a fragment thereof, and may be identified by methods such as screening large libraries of compounds (Beck-Sickinger & Weber (2001) Combinational Strategies in Biology and Chemistry (John Wiley & Sons, Chichester, Sussex); by structure-activity relationship by nuclear magnetic resonance (Shuker et al (1996) "Discovering high-affinity ligands for proteins: SAR by NMR. Science 274: 1531-1534); encoded self-assembling chemical libraries Melkko et al (2004) "Encoded self-assembling chemical libraries." Nature Biotechnol. 22: 568-574); DNA-templated chemistry (Gartner et al (2004) "DNA-tem plated organic synthesis and selection of a library of macrocycles. Science 305: 1601-1605); dynamic combinatorial chemistry (Ramstrom & Lehn (2002) "Drug discovery by dynamic combinatorial libraries." Nature Rev. Drug Discov. 1: 26-36); tethering (Arkin & Wells (2004) "Small-molecule inhibitors of protein-protein interactions: progressing towards the dream. Nature Rev. Drug Discov. 3: 301-317); and speed screen (Muckenschnabel et al (2004) "SpeedScreen: label-free liquid chromatography-mass spectrometry-based high-throughput screening for the discovery of orphan protein ligands." Anal. Biochem. 324: 241-249). Typically, small molecules will have a dissociation constant for KIT in the nanomolar range.

Exemplary small molecule inhibitors of KIT include but are not limited to indolinones, pyrimidine derivatives, pyrrolopyrimidine derivatives, quinazoline derivatives, quinoxaline derivatives, pyrazoles derivatives, bis monocyclic, bicyclic or heterocyclic aryl compounds, vinylene-azaind 1e derivatives and pyridylquinolones derivatives, styryl compounds, styryl-substituted pyridyl compounds, seleoindoles, selenides, tricyclic polyhydroxylic compounds, benzylphosphonic acid compounds, and any combinations thereof.

Without limitations, the KIT inhibitors can include antibodies and other agents that bind to SCF and inhibit or reduce its binding to KIT. Examples of SCF antibodies are described in U.S. Pat. No. 7,144,731; and U.S. Patent Application No. US2005/0261175, the relevant disclosures of which are incorporated herein by reference for the intended purpose.

The capability of a candidate compound, such as a small molecule, protein, or peptide, to bind to or interact with a KIT or SCF polypeptide or fragment thereof may be measured by any method of detecting/measuring a protein/protein interaction or other compound/protein interaction. Suitable methods include methods such as, for example, yeast two-hybrid interactions, co-purification, ELISA, co-immunoprecipitation and surface plasmon resonance methods. Thus, the candidate compound may be considered capable of binding to the polypeptide or fragment thereof if an interaction may be detected between the candidate compound and the polypeptide or fragment thereof by ELISA, co-immunoprecipitation or surface plasmon resonance methods or by a yeast two-hybrid interaction or co-purification method, all of which are known in the art. Screening assays which are capable of high throughput operation are also contemplated. Examples may include cell based assays and protein-protein binding assays.

II. Therapeutic Applications

Any of the KIT inhibitors, e.g., those described herein, can be used for conditioning a subject for a hematopoietic stem cell (HSC) transplantation. As used herein the term "conditioning" in the context of a patient pretreatment in need of HSC transplanation typically means destroying substantially the bone marrow and immune system of the patient by a suitable procedure, for example, treatment with an KIT inhibitor.

The subject to be treated by the methods described herein can be a human (i.e., a male or a female of any age group, for example, a pediatric subject (e.g., an infant, child, or an adolescent) or an adult subject (e.g., a young adult, a middle-aged adult, or a senior adult)). The subject may also include any non-human animals including, but not limited to a non-human mammal such as cynomolgus monkey or a rhesus monkey. In certain embodiments, the non-human animal is a mammal, a primate, a rodent, an avian, an equine, an ovine, a bovine, a caprine, a feline, or a canine. The non-human animal may be a male or a female at any stage of development. The non-human animal may be a transgenic animal or a genetically engineered animal. A "patient" refers to a human subject in need of treatment of a disease.

In some embodiments, the subject (e.g., a human subject) is hypersensitive to a DNA damaging agent, which can be any agent that directly or indirectly induces any type of DNA damage in a cell. DNA damage can include, e.g., strand breaks, dimerization or cross-linking, unpaired bases, modified bases, conversion of one base into another resulting in unpaired bases, chromatin unwinding or other modifications, etc. Exemplary DNA damaging agents include, but are not limited to alkylating agents (e.g., cyclophosphamide, and busulfan), irradiation (e.g., UV, gamma, X-ray), DNA cross-linking agents, antibiotics that induce DNA damage by binding to DNA, inhibitors of topoisomerase, and any compound used in chemotherapy which acts by causing DNA damage.

Exposure of cells/tissue to a DNA damaging agent can cause DNA damage, resulting in molecular lesions. Some of these can lesions cause structural damage to the DNA molecule and can alter or hinder the cell's ability to transcribe the gene that the affected DNA encodes. Some lesions can induce potentially harmful mutations in the cell's genome, which affect the survival of its daughter cells after it undergoes mitosis. Functional DNA repair mechanism in cells can generally repair these lesions and/or recover the lost DNA information after exposure to a DNA damaging agent. However, a defect in DNA repair mechanism may result in a complete failure in repairing DNA damage or lesions, or a reduced rate of DNA repair as compared to the repair rate of a functional DNA repair mechanism. Thus, cells with a defect in DNA repair mechanism may have a high accumulation of DNA damage, resulting in a higher likelihood to become senescent, apoptotic, or mutated (e.g., cancerous), as compared to cells with functional DNA repair mechanism.

Subjects who are hypersensitive to at least one DNA damaging agent are abnormally susceptible physiologically to the DNA damaging agent. For example, such a DNA damaging agent may cause side effects in such subjects at a much higher level, at much lower doses, or both, as compared with normal subjects. Subjects who are hypersensitivity to DNA damaging agents may have one or more defects in the DNA repairing system such that they have a lower ability to repair DNA damages caused by the agent. As such, they may have an increased risk of experiencing adverse effects associated with a DNA damaging agent after exposure to a DNA damaging agent, as compared to the risk observed in subjects with functional DNA repair mechanism (e.g., healthy subjects). Exemplary adverse effects associated with a DNA damaging agent include, but are not limited to infertility, cataracts, endocrinopathies, tumorigenesis, and/or development of complications (e.g., increased malignancy of a disease or disorder, e.g., fanconi anemia).

In some embodiments, the subject may have a genetic defect in a gene involved in DNA repair. Examples of such genes include, but are not limited to, BRCA1, BRCA2, ataxia telangiectasia mutated (ATM), Nijmegen breakage syndrome (NBS), MRE11A, Bloom syndrome (BLM), WRN, RECQL4, Fanconi anemia genes (e.g., FANCA, B, C, D1, D2, E, F, G, I, J, K, M, N), XPC, XPA, XPB, XPD, XPF, XPG, XPV, and TP53.

The subject may be a human patient having a disease or disorder associated with impaired DNA repairing system, for example, fanconi anemia, ataxia telangiectasia, bloom syndrome, cockayne's syndrome, progeria, Rothmund-Thomson Syndrome, Trichothiodystrophy, Werner Syndrome, and Zeroderma pigmentosum.

In some examples, the subject is free of other pretreatments prior to HSC transplanation, such as irradiation or other conditioning regimens, e.g., those involving the use of a DNA damaging agent.

To perform the methods described herein, an effective amount of a KIT inhibitor (e.g., those described herein) can be administered to a subject in need of the treatment via a suitable route.

An "effective amount," "effective dose," or an "amount effective to", as used herein, refers to an amount of a KIT inhibitor as described herein that is effective in producing the desired therapeutic, ameliorative, inhibitory or preventative effect, and/or results in a desired clinical effect, such as increased engraftment of HSCs in a subject after HSC transplantation. Effective amounts vary, as recognized by those skilled in the art, depending on route of administration, excipient usage, and co-usage with other active agents.

In the case of treating a particular disease or condition characterized by a defect in DNA repair, the desired response is inhibiting the progression of the disease. This may involve only slowing the progression of the disease temporarily, although more preferably, it involves halting the progression of the disease permanently. This can be monitored by routine methods or can be monitored according to diagnostic methods of the invention discussed herein. The desired response to treatment of the disease or condition also can be delaying the onset or even preventing the onset of the disease or condition.

Such amounts will depend, of course, on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

For example, an effective amount of a KIT inhibitor described herein when administered to a subject results in, e.g., increased engraftment of HSCs in a subject after HSC transplantation by at least about 10% or more, including, e.g., at least about 20%, at least about 30%, at least about 40%, at least about 50%, at least about 60%, at least about 70%, at least about 80%, at least about 90% or more, as compared to engraftment of HSCs without conditioning with a KIT inhibitor. In some embodiments, an effective amount of a KIT inhibitor described herein when administered to a subject results in, e.g., increased engraftment of HSCs in a subject after HSC transplantation by at least about 1.1-fold or more, including, e.g., at least about 2-fold at least about 3-fold, at least about 4-fold, at least about 5-fold, at least about 6-fold, at least about 7-fold, at least about 8-fold, at least about 9-fold, at least about 10-fold or more, as compared to engraftment of HSCs without conditioning with a KIT inhibitor.

An effective dose of an KIT inhibitor for the methods described herein can be between 5 mg/kg and 100 mg/kg, or between 10 mg/kg and 80 mg/kg, or between 20 mg/kg and 60 mg/kg. A physician in any event may determine the actual dosage which will be most suitable for any subject, which will vary with the age, weight and the particular disease or disorder to be treated or prevented. For example, an effective dose of an KIT inhibitor can be administered to a subject in need of a HSC transplantation daily, every 2 days, every 3 days, or longer, prior to the subject receiving a HSC transplantation.

In some embodiments, at least one or more KIT inhibitors are formulated for administration to a subject as a pharmaceutical composition, e.g., together with a pharmaceutically acceptable carrier, diluent or excipient.

A carrier, diluent or excipient that is "pharmaceutically acceptable" includes one that is sterile and pyrogen free. Suitable pharmaceutical carriers, diluents and excipients are well known in the art. The carrier(s) must be "acceptable" in the sense of being compatible with the inhibitor and not deleterious to the recipients thereof.

A pharmaceutical composition comprising any of the KIT inhibitors described herein (e.g., 1, 2, 3 or more KIT inhibitors described herein) may be administered by any administration route known in the art, such as parenteral administration, oral administration, buccal administration, sublingual administration, topical administration, or inhalation, in the form of a pharmaceutical formulation comprising the active ingredient, optionally in the form of a non-toxic organic, or inorganic, acid, or base, addition salt, in a pharmaceutically acceptable dosage form. In some embodiments, the administration route is oral administration and the formulation is formulated for oral administration.

In some embodiments, the pharmaceutical compositions or formulations are for parenteral administration, such as intravenous, intra-arterial, intra-muscular, subcutaneous, or intraperitoneal administration.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. Aqueous solutions may be suitably buffered (preferably to a pH of from 3 to 9). The preparation of suitable parenteral formulations under sterile conditions is readily accomplished by standard pharmaceutical techniques well-known to those skilled in the art.

In some embodiments, the pharmaceutical composition or formulation is suitable for oral, buccal or sublingual administration, such as in the form of tablets, capsules, ovules, elixirs, solutions or suspensions, which may contain flavoring or coloring agents, for immediate-, delayed- or controlled-release applications.

Suitable tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxy-propylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavoring agents, coloring matter or dyes, with emulsifying and/or suspending agents and with diluents such as water, ethanol, propylene glycol and glycerin, and combinations thereof.

In some embodiments, the pharmaceutical composition or formulation is suitable for intranasal administration or inhalation, such as delivered in the form of a dry powder inhaler or an aerosol spray presentation from a pressurized container, pump, spray or nebulizer with the use of a suitable propellant, e.g. dichlorodifluoromethane, trichlorofluoromethane, dichlorotetrafluoro-ethane, a hydrofluoroalkane, carbon dioxide or other suitable gas. In the case of a pressurized aerosol, the dosage unit may be determined by providing a valve to deliver a metered amount. The pressurized container, pump, spray or nebulizer may contain a solution or suspension of the active compound, e.g. using a mixture of ethanol and the propellant as the solvent, which may additionally contain a lubricant. Capsules and cartridges (made, for example, from gelatin) for use in an inhaler or insufflator may be formulated to contain a powder mix of the inhibitor and a suitable powder base such as lactose or starch.

In some embodiments, the pharmaceutical compositions or formulations are suitable for topical administration to a subject. The inhibitor may be applied topically in the form of a lotion, solution, cream, ointment or dusting powder, or may be transdermally administered, for example, by the use of a skin patch. For application topically to the skin, the inhibitor can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water. Formulations suitable for topical administration in the mouth include lozenges comprising the active ingredient; pastilles comprising the active ingredient in an inert basis such as gelatin and glycerin, or sucrose and acacia; and mouth-washes comprising the active ingredient in a suitable liquid carrier. See, e.g., Remington: The Science and Practice of Pharmacy 20th Ed. (2000) Lippincott Williams and Wilkins, Ed. K. E. Hoover.

The formulations may be presented in unit-dose or multi-dose containers, for example sealed ampoules or vials, and may be stored in a freeze-dried (lyophilized) condition requiring only the addition of the sterile liquid carrier immediately prior to use.

In some embodiments, the formulations can be pre-loaded in a unit-dose injection device, e.g., a syringe, for intravenous injection.

In some embodiments, the KIT inhibitor can be administered to a subject at a dose of between 0.1 to 1,000 mg per subject or between 0.001 to 10 mg/kg per subject, administered in single or divided doses. An effective dose of an KIT inhibitor for the methods described herein can be between 5 mg/kg and 100 mg/kg, or between 10 mg/kg and 80 mg/kg, or between 20 mg/kg and 60 mg/kg. A physician in any event may determine the actual dosage which will be most suitable for any subject, which will vary with the age, weight and the particular disease or disorder to be treated or prevented. For example, an effective dose of an KIT inhibitor can be administered to a subject in need of a HSC transplantation daily, every 2 days, every 3 days, or longer, prior to receiving the HSC transplantation.

Vectors encoding an KIT inhibitor may be administered to a subject using any method known in the art, such as using liposomes, viral vectors (including vaccinia, modified vaccinia, adenovirus, retrovirus, lentivirus, and adeno-associated viral (AAV) vectors), and by direct delivery of the vector.

In any aspects of the methods described herein, a second effective dose of an inhibitor of KIT may be administered to the subject after the first dose, when desirable, e.g., to increase the circulation time of the KIT inhibitor in the subject. The inhibitor of KIT in the second dose can be the same or different from the one in the second dose. The second dose can be same as, or higher or lower than, the first dose.

After administration of the inhibitor of KIT, a first population of HSCs are transplanted to the subject. Preferably, a first population of HSCs is transplanted to the subject after the inhibitor of KIT is substantially cleared from serum of the subject. For example, a first population of HSCs can be transplanted to the subject after the measured serum concentration of the KIT inhibitor is below a detectable level. Alternatively, a first population of HSCs can be transplanted to the subject after the measured serum concentration of the KIT inhibitor is too low to induce any significant SCF-mediated HSC proliferation in an in vitro assay, as compared to HSC proliferation in vitro in the absence of a KIT inhibitor. In some embodiments, a first population of HSCs can be transplanted to the subject when the serum concentration of the KIT inhibitor is no more than 0.5 mg/ml, 0.4 mg/ml, 0.3 mg/ml, 0.2 mg/ml, 0.1 mg/ml, 0.05 mg/ml, 0.025 mg/ml, 0.01 mg/ml, 0.005 mg/ml, 0.0025 mg/ml, 0.001 mg/ml, 0.0005 mg/ml, 0.0001 mg/ml or lower. The kinetics of the clearance of a KIT inhibitor in a subject can be determined by collecting a blood or serum sample from the subject and detecting for the presence of the KIT inhibitor in the serum sample using any methods known in the art, e.g., in vitro functional assays such as assessment of SCF-mediated HSC proliferation or direct measurement of the amount of the KIT inhibitor in the serum sample, e.g., using immunoassay.

The period of time for clearance of the KIT inhibitor in serum of a subject can vary with each individual (e.g., depending on his/her age and/or weight, dose of a KIT inhibitor administered, and/or administration method). Thus, in some embodiments, the first population of HSCs can be transplanted to the subject at least 24 hours after the administration of the inhibitor of KIT. In some embodiments, the first population of HSCs can be transplanted to the subject at least 3 days or longer, including, e.g., at least 4 days, at least 5 days, at least 6 days, at least 7 days, at least 8 days, at least 9 days, at least 10 days, at least 12 days, at least 14 days, at least 16 days, at least 18 days, at least 20 days or longer, after the administration of the inhibitor of KIT.

It was discovered that administration of an inhibitor of KIT alone is sufficient to permit effective engraftment of donor HSCs after transplantation. Accordingly, the subject who is conditioned with an inhibitor of KIT is not required to receive any further conditioning treatment, e.g., irradiation treatment or administration of a DNA damaging agent, before a HSC transplantation.

Where it is desirable, the subject can further receive a second HSC transplantation after the transplantation of the first population of HSCs. The second HSC transplantation can be performed any time after the first HSC transplantation. For example, the second HSC transplantation can be performed about 3 days or longer, including 4 days, 5 days, 6 days, 7 days, 2 weeks, 3 weeks, 4 weeks, or longer, after the first HSC transplantation.

In any methods described herein, the HSCs for transplantation can be derived from bone marrow, peripheral blood cells, and/or umbilical cord blood. Alternatively, the HSCs can be derived from stem cells (e.g., induced pluripotent stem cells which can be differentiated from somatic cells such as skin cells). The HSCs can be cultured ex vivo prior to transplantation to a subject.

In some embodiments, the HSCs may be isolated from the same subject (autologous), cultured ex vivo when needed, and be transplanted back to the subject. Alternatively, the HSCs can be allogenic, i.e., obtained from a different subject of the same species. For allogeneic HSC transplantation, allogeneic HSCs may have a HLA type that matches with the recipient.

The HSCs can be genetically modified prior to transplantation to the subject. By way of example only, autologous HSCs collected from a fanconi anemia (FA) patient are abnormal, e.g., FA HSCs typically having lower KIT expression, an up-regulation of genes associated with apoptosis, senescence, and inflammatory signaling, and/or a down-regulation of genes associated with stress-handling/survival. These abnormal autologous HSCs can be genetically modified or corrected to permit an autologous HSC transplantation.

In aspect, the method described herein can be applied to treat fanconi anemia or other diseases associated with defective DNA repairing system and needs HSC transplantation.

Fanconi anemia (FA) is one of the common causes of inherited bone marrow failure (BMF). Currently, hematopoietic stem cell (HSC) transplantation is the only therapeutic option for the BMF. Alkylating chemotherapy and/or irradiation have been conventionally used to condition FA patients for a HSC transplantation. However, due to the underlying defect in DNA repair mechanism, FA patients generally have inherent hypersensitivity to DNA damaging agents, e.g., DNA cross-linking/alkylating agents such as cyclophosphamide, busulfan and irradiation. Thus, these FA patients tolerate alkylating chemotherapy and/or irradiation-based conditioning poorly, which results in high acute peri-transplant morbidity and/or mortality. Additionally, exposure of cells/tissues to alkylating agents in FA patients increases their long-term risk of secondary malignancies such as increased secondary squamous cell carcinoma. In accordance with one aspect of the disclosure described herein, an inhibitor of KIT, which is not an alkylating agent, can be administered to FA patients as a conditioning agent for a HSC transplantation to decrease the morbidity and mortality associated with HCS transplantation in FA patients. The method described herein can be used to treat fanconi anemia.

The term "treating" as used herein refers to the application or administration of a composition including one or more active agents to a subject, who has a target disease (e.g., FA), a symptom of the target disease, or a predisposition toward the target disease, with the purpose to cure, heal, alleviate, relieve, alter, remedy, ameliorate, improve, or affect the disease, the symptoms of the disease, or the predisposition toward the disease.

To perform the method described herein, an effective amount of an KIT inhibitor can be administered to a human patient having FA via a suitable route. One or more populations of HSCs can then be transplanted into the patient. The KIT inhibitor could induce apoptosis of the endogenous HSCs and then enhance engraftment of the donor HSCs, thereby effective in treating FA.

III. Kits for use in Conditioning Subjects for HSC Transplantation

The present disclosure also provides kits for use in conditioning a subject in need of the treatment (e.g., an FA patient) for HSC transplantation. Such kits can include one or more containers comprising an inhibitor of KIT, and optionally, one or populations of HSC cells.

In some embodiments, the kit can comprise instructions for use in accordance with any of the methods described herein. The included instructions can comprise a description of administration of the KIT inhibitor for conditioning a subject for HSC transplantation as described herein. The kit may further comprise a description of selecting an individual suitable for treatment based on identifying whether that individual is, e.g., sensitive to DNA damaging agents and/or having FA or other related diseases. In still other embodiments, the instructions comprise a description of administering the KIT inhibitor and/or the HSCs to an individual in need of the treatment.

The instructions relating to the use of an KIT inhibitor generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for conditioning subject for HSC transplantation. Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an KIT inhibitor as those described herein.

Kits may optionally provide additional components such as buffers and interpretive information. Normally, the kit comprises a container and a label or package insert(s) on or associated with the container. In some embodiments, the invention provides articles of manufacture comprising contents of the kits described above.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1

KIT Blockade is Sufficient to Sustain Donor Hematopoietic Stem Cell Engraftment in Fanconi Anemia Mice Fanconi anemia (FA) is the most common cause of inherited bone marrow failure (BMF), with allogenic hematopoietic stem cell transplant (HSCT) as the only curative option. However due to the underlying DNA repair defect, FA patients poorly tolerate alkylating chemotherapy-conditioning, which is necessary for donor engraftment, but results in high acute peri-transplant morbidity/mortality, and further augments their inherent increased risk of malignancies.

It is presented herein that FA hematopoietic stem/progenitor cells (HSPC) had several features that indicated their increased susceptibility to KIT blockade-mediated killing. For example, KIT expression was lower in FA HSPC while KIT-ligand expression was higher in FA stroma, indicating increased KIT-signaling; genes associated with apoptosis, senescence and inflammatory signaling were upregulated and those associated with stress-handling/survival were downregulated in FA-HSPC. As shown herein, FA-HSPC demonstrated increased susceptibility to blocking KIT antibody (KIT-Ab)-mediated killing in vitro. Definitive HSCT in FA mice using KIT-Ab based conditioning resulted in significant normal donor HSC engraftment, with multilineage chimerism that progressively increased to ~25% by 4-months and was sustained in secondary transplants. Chimerism further increased up to 48% following Alum-mediated inflammatory stress. Overall, it is shown that KIT-blockade alone is an adequate non-genotoxic, HSPC-targeted conditioning in FA mice; its clinical translation can circumvent the extensive transplant-related morbidity/mortality in this disease.

Exemplary Methods and Materials

The assessment of hematopoietic compartments and HSPC analysis was assessed in 8-12 week-old FancA-KO, FancD2-KO and WT mice. Definitive HSCT from CD45.1 congenic donors were performed on day 7 following ACK2 while some animals were sacrificed at day 7 to assess HSPC depletion. Donor chimerism was assessed by monthly bleeds and BM assessment at sacrifice at 4 months, when secondary transplants were performed. Some primary mice were subjected to inflammatory stress by Alum injections. Hu et al. *The Journal of clinical investigation*. 2013; 123(9):3952-66.

Mice

All mice were housed, bred and studied under pathogen free conditions using protocols approved by the IACUC (Institutional Animal Care and Use Committee) in the Cincinnati Children's Research Foundation Vivarium. The mice referred to as wild type (WT), C57BL/6 (CD45.2$^+$) mice and B6.SJL-PtrcaPep3b/BoyJ (CD45.1$^+$) mice were purchased from Jackson laboratory.

In Vitro Studies

Bone marrow cells from both WT and FA$^{-/-}$ mice were stained with antibodies against Lineage markers, c-Kit, Sca-1, CD150, and CD48 respectively to access the different BM compartments such as LSK (Lin−, Sca-1+ and KIT+) cells and LSK-SLAM (CD150+ and CD48−). KIT expression was evaluated in both LSK and also in Lineage negative side population. Side population staining was done using previously described standard protocol. Goodell et al. *Nature medicine*. 1997; 3(12):1337-45. For both apoptosis studies, sorted LSK cells of WT and FA$^{-/-}$ were incubated for 48 hours in Ex-vivo 10 medium with 50 ng/ml of SCF and TPO with or without a blocking KIT antibody (e.g., ACK2) at a concentration of about 20 mg/ml. Apoptosis was assessed with Annexin-V and 7AAD. HSPC senescence was assessed in sorted LSK following incubation 48 hours in Ex-vivo 10 medium with 50 ng/ml of SCF and TPO by C12FDG staining. Cho et al. *The Journal of clinical investigation*. 2014; 124(7):3159-71. Baseline cell cycle analysis was done in different bone marrow compartments using Ki-67 and Hoechst 33342 as previously described. Kunisaki, et al. *Nature*. 2013; 502(7473):637-43.

In-Vivo HSC Depletion and Transplant

Day 7 following ACK2 injection of 40 mg/kg i.p, depletion of HSPC was evaluated by flow cytometric enumeration and CFU assay. Mice aging 8-12 weeks were used for transplant experiments. Twenty million whole bone marrow cells (WBM) harvested from the donor (WT BoyJ) mice was transplanted into C57BL/6, FA$^{-/-}$ and FD$^{-/-}$ mice on Day 7 following saline or 40 mg/kg of intraperitoneal injection of ACK2. Secondary hematopoietic cell transplant (HCT) was performed using 5 million cells from the primary transplant mice to lethally irradiated F1 mice (double positive CD45.1/CD45.2). Peripheral blood samples was stained with anti CD45.1$^+$-APC, anti CD45.2$^+$-PE and anti Gr-1$^+$- to determine donor blood chimerism in whole WBC and Granulocyte compartment using FACS Canto instrument (BD Biosciences) at 4, 12 and 16 weeks.

RNA Isolation, Sequencing and qRT-PCR

Total RNA from sorted WT and FA$^{-/-}$ LSK cells was extracted using Trizol method. Brattelid et al. *Basic research in cardiology*. 2007; 102(3):198-208. and subjected to Illumina TruSeq kit RNA V2 library generation. Sequencing was done at a depth 20 million paired-end 50 base reads on an Illumina HiSeq 2000. FASTQ files were aligned to the human genome build GRCh37 and University of California Santa Cruz (UCSC) transcriptome reference (Karolchik et al. *Nucleic Acids Res.* 2014; 42(D1):D764-D770) using Tophat 2.0.9 (Kim et al. *Genome biology.* 2013; 14(4):R36) and Bowtie2 (Langmead et al. *Genome biology.* 2009; 10(3):R25). Gene-level FPKM expression was also obtained with Cufflinks2. Trapnell et al. *Nature protocols.* 2012; 7(3):562-78. (ccb.jhu.edu/software/tophat/igenomes.shtml). RNA was also extracted from WT and FA$^{-/-}$ bone marrow stromal cells (CD45 negative Ter-119 negative cells). Quantitative real-time PCR was done for KIT-ligand (SCF) using Taqman primer/probe set from life technologies (Mm00442972_m1).

ELISA for SCF

Femur from both WT and FA$^{-/-}$ mice was crushed in 5 ml of IMDM (Lonza; catalog number 12-722F) and ELISA for SCF was done from the supernatant using R&D ELISA Kit (catalog number, MCK00) as per manufacturers' recommendations.

Results and Discussion

Total BM cellularity was comparable between WT and FancA (FA$^{-/-}$) mice (FIG. 1, panel a). However, the absolute numbers of HSPCs were significantly decreased in FA$^{-/-}$ mice, with a very significant reduction in the Lin-Sca+Kit+ (LSK) cell compartment, and a significant, albeit less remarkable reduction in the more primitive LSK-SLAM or the 'HSC' compartment (FIG. 1, panel b). Without wishing to be bound by theory, there would be a replicative stress due to attrition of HSPC compartment. FIG. 1, panel d shows that the entire HSPC compartment had a significantly higher cycling status than the WT HSPC counterpart. See also, Li et al. *Blood.* 2003; 102(6):2081-4.

Figure 3:
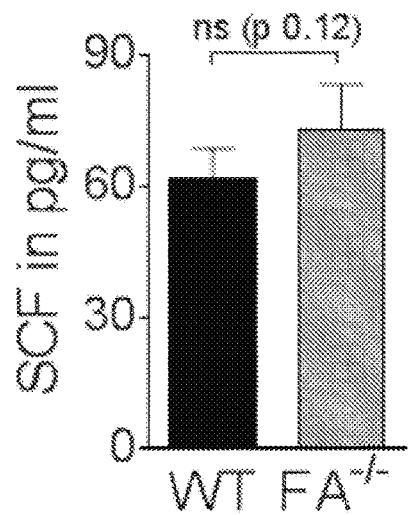
FIG. 3 shows that SCF levels appeared to be higher in FA bone marrow. SCF levels were determined by ELISA from supernatant from bone marrow from WT and FA mice (WT n=4, FA$^{-/-}$ n=65).
Figure 4:
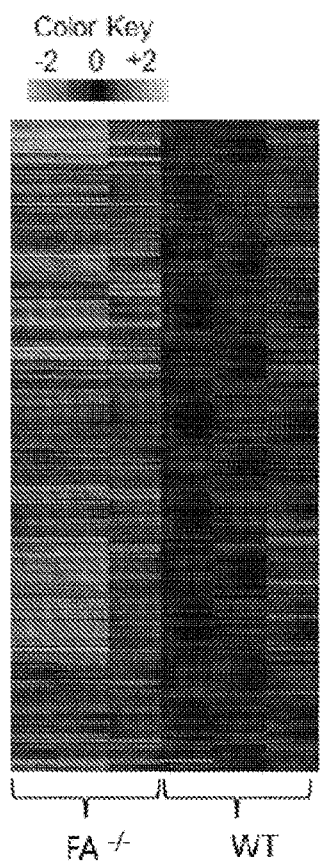
FIG. 4 shows the transcriptional profile of FA LSK cells and the exemplary gene ontology pathways affected. Heat map of differently expressed genes (left panel) and pathways (right table) between WT and FA$^{-/-}$ LSK cells is shown with arrows indicating upregulated or downregulated genes (n=3).

Another prominent feature of FA$^{-/-}$ HSPC was their significantly reduced KIT expression. This was evident in both on the LSK cells and the lineage-negative side population (SP) cells (FIG. 1, panels e to h). Conversely, expression of the KIT-ligand, stem cell factor (SCF) was upregulated in FA$^{-/-}$ BM stroma (FIG. 1, panel i), with increased SCF levels in bone marrow supernatant (FIG. 3), indicating that KIT signaling was upregulated in FA HSPC. Furthermore, mRNA expression of pro-apoptotic, senescence and inflammatory genes was upregulated and conversely, genes associated with stress/survival were downregulated in FA LSK cells (FIG. 1, panels j and k; and FIG. 4). FA LSK cell compartment showed increased proportion of apoptotic and senescent cells under proliferative stress in vitro, compared to WT LSK cells (FIG. 1, panels l to o). Collectively, these data indicated that FA HSPC can be more susceptible to KIT blockade-mediated conditioning.

Figure 2:
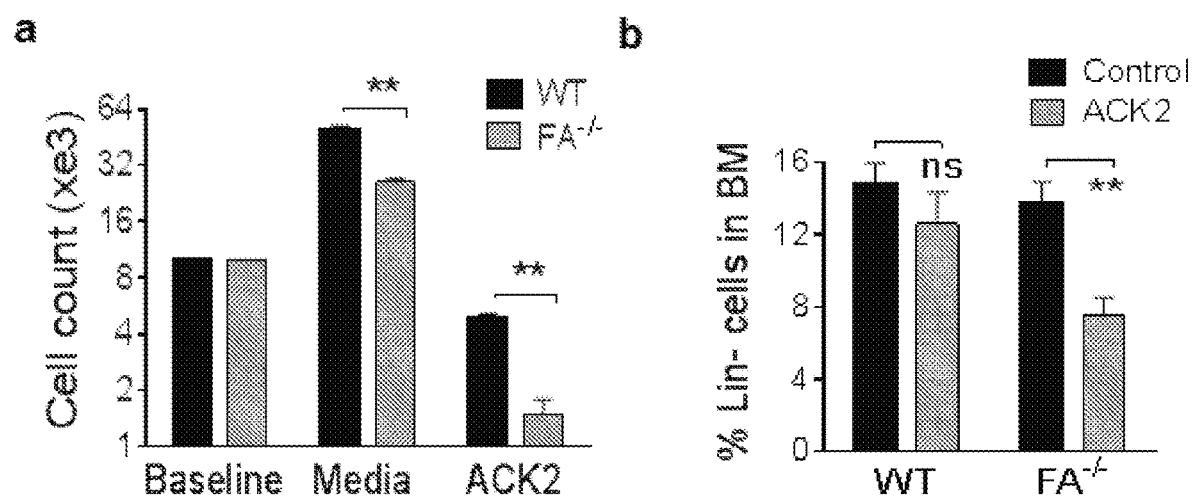
FIG. 2 includes diagrams showing that targeting KIT signaling alone in FANC mice resulted in significant reduction in FA HSPC to allow a clinically useful engraftment of WT donor HSPC. (Panel a) 10000 LSK cells were sorted and cultured for 72 hours in Ex-vivo 10 containing 100 ng/ml of SCF and 100 ng/ml of TPO with or without 50 mcg/ml of a blocking KIT antibody (e.g., ACK2). Cell counts were then quantified (n=1; 3 independent experiments). (Panels b and c) Represents percentage of lineage negative cells (Sal WT n=8; ACK2 WT n=3; Sal FA$^{-/-}$, n=5; ACK2 FA$^{-/-}$, n=3) and CFU count per 1e5 BM cells accessed 7 days following 40 mg/kg i.p. injection of ACK2 (WT n=6, FA$^{-/-}$, n=6). (Panel d) Donor PB chimerism at 16 weeks (Sal WT n=5; ACK2 WT n=6; Sal FA$^{-/-}$, n=4 ACK2 FA$^{-/-}$, n=6) (Panel e) Represents donor chimerism in different bone marrow compartments and peripheral blood at 16 weeks (n=4). (Panel f) Percentage donor chimerism in secondary HCT (WT n=6, FA$^{-/-}$, n=16). (Panel g) Temporal progression of PB donor chimerism from 4 weeks to 16 weeks post HCT and shows the effect of donor chimerism post Alum challenge (WT n=3, FA$^{-/-}$, n=6 in all time point except WT n=4, FA$^{-/-}$, n=3 in 28 week). **P<0.0001, *P<0.001, **P<0.01, *P<0.05 (Student t test, one way (Panel e) and two way ANOVA (Panel d)).
Figure 2:
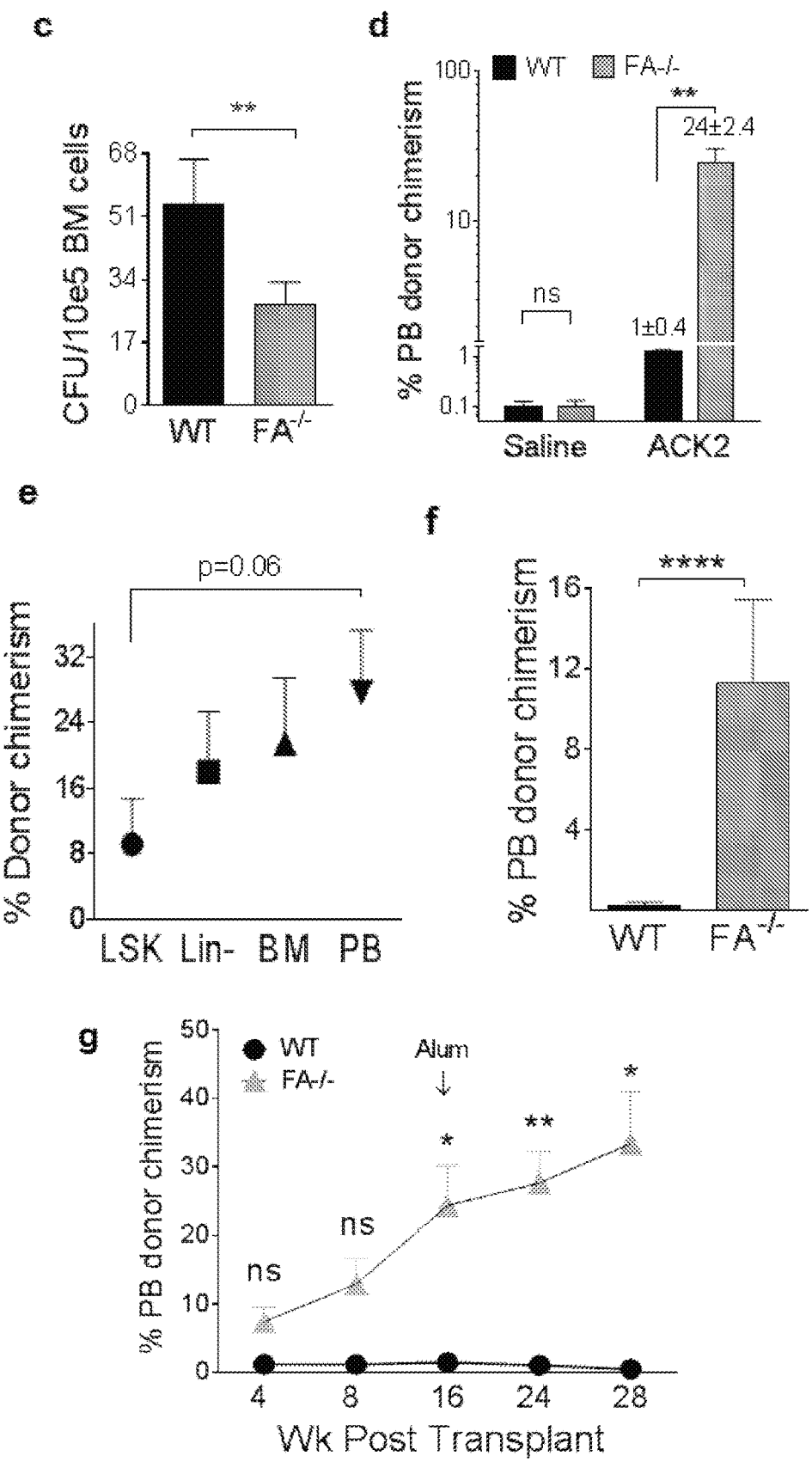
Figure 5:
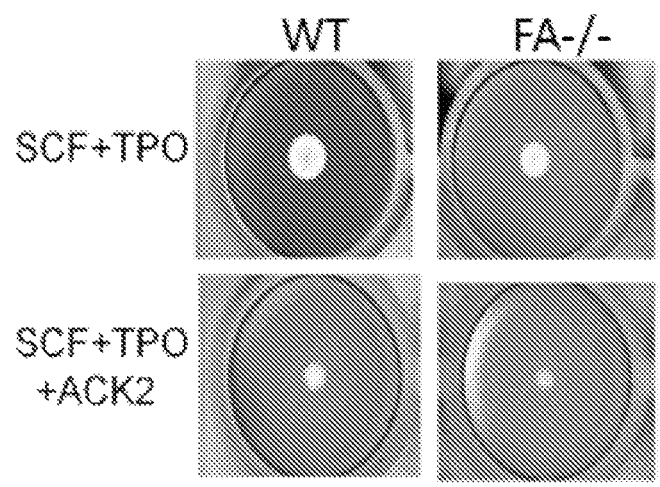
FIG. 5 shows the impaired expansion of FA LSK cells under proliferative stress. (Panel a) 10000 LSK cells were sorted and cultured for 72 hours in EX vivo-10 containing 100 ng/ml of SCF and 100 ng/ml of TPO with or without 50 mcg/ml of a blocking KIT antibody (e.g., ACK2). A set of representative images of the cell pellets is shown. Panel b shows absolute cells counts in WT and FANCA$^{-/-}$ after 72 hours in culture.
Figure 5:
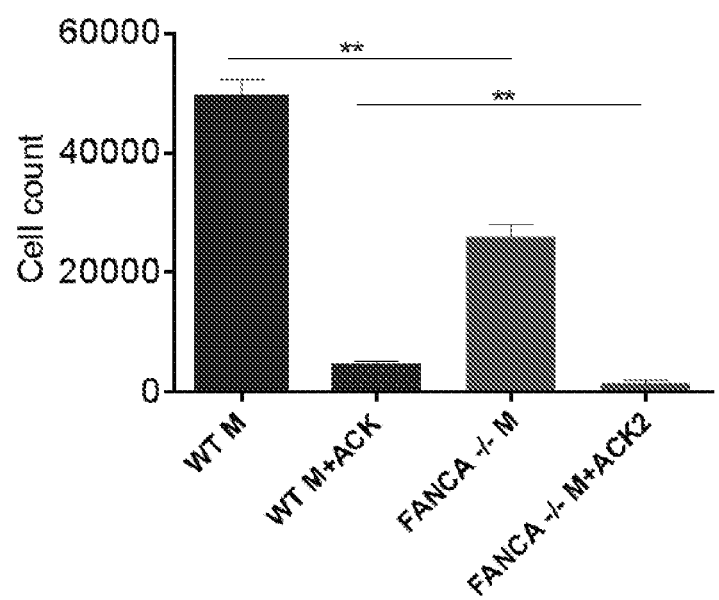
Figure 6:
FIG. 6 shows experimental data for KIT-based antibody pretreatment followed by a HSC transplant. Panel a shows an example experimental treatment protocol for FA$^{-/-}$ and FD$^{-/-}$ mice. Panel b shows CFU count per 1e5 BM cells accessed 7 days following 40 mg/kg i.p. injection of a blocking KIT antibody (e.g., ACK2) in FANCD (FD$^{-/-}$) mice (WT Control and Saline n=3 each, FD$^{-/-}$ Control and Saline n=3 each). Panel c shows PB donor chimerism at 16 weeks post HCT in FD$^{-/-}$ mice (n=4 in each group except 28 week ACK2 n=2).
Figure 6:
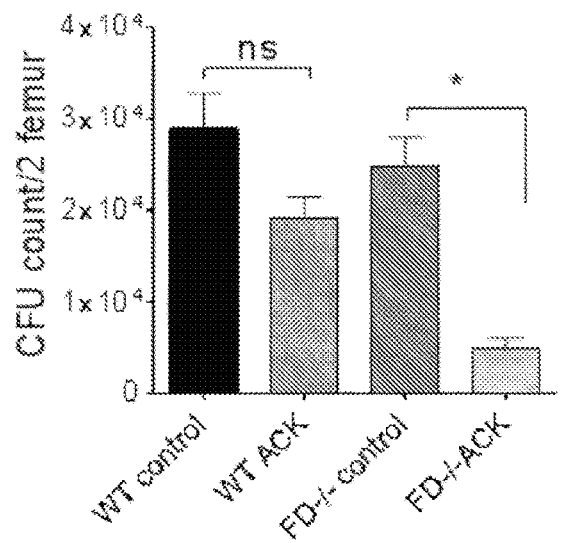
Figure 6:
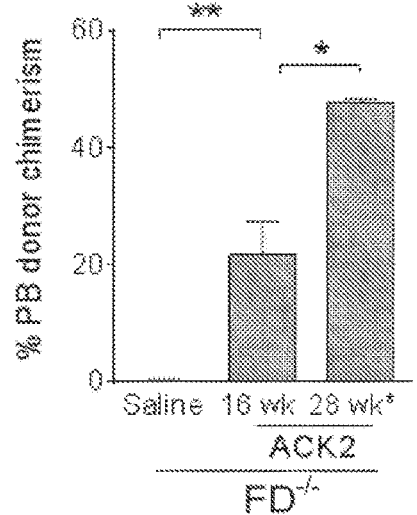
Figure 7:
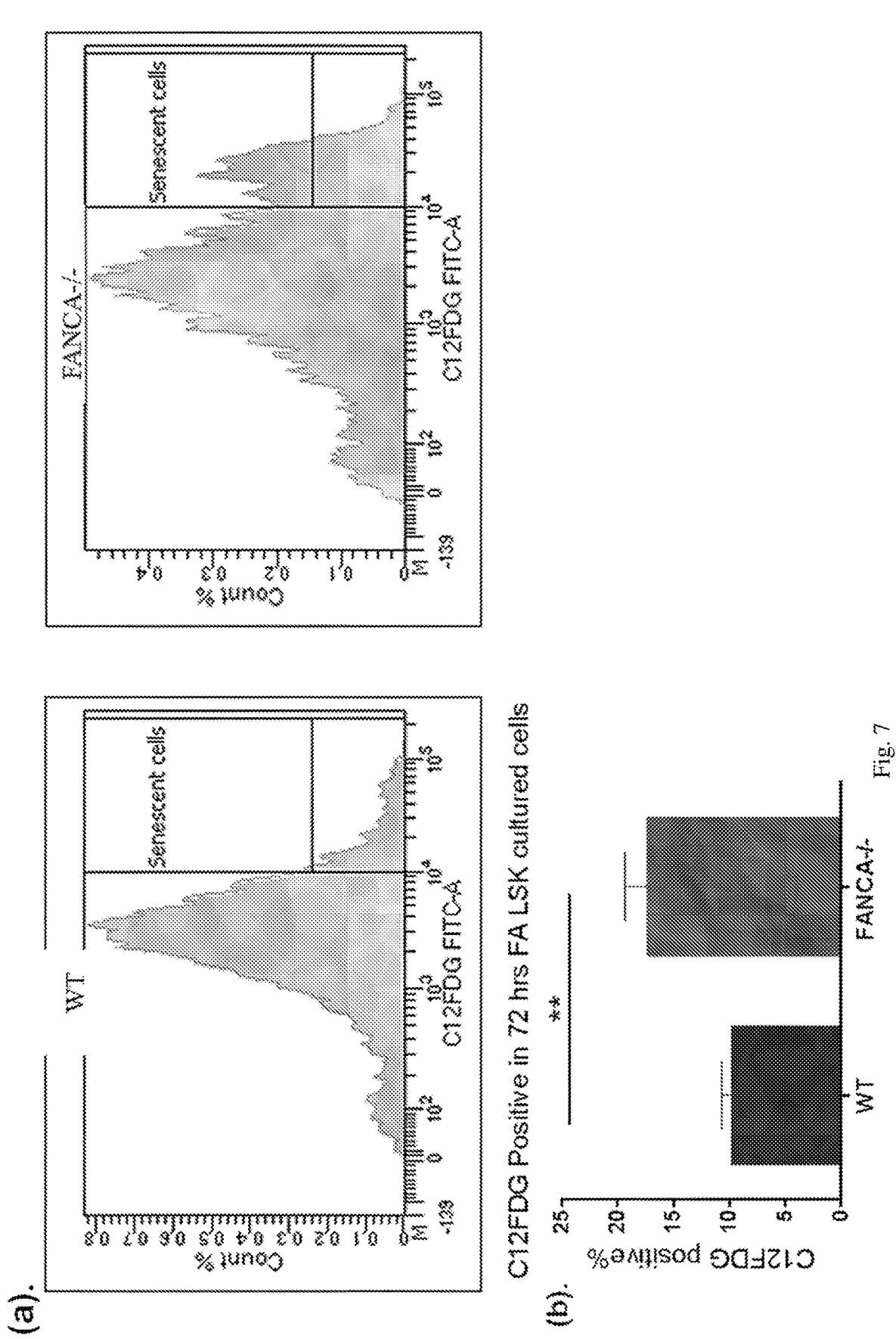
FIG. 7 shows that FANCA$^{-/-}$ hematopoietic stem/progenitor cells (HSPCs) in culture showed higher senescence. Panel a shows that percent of sorted LSK from WT and FANC$^{-/-}$ mice were cultured in SCF+TPO containing media for 72 hours and stained for C12FDG. Panel b shows quantified percent senescent cells in WT and FANCA$^{-/-}$ mice.
Figure 8:
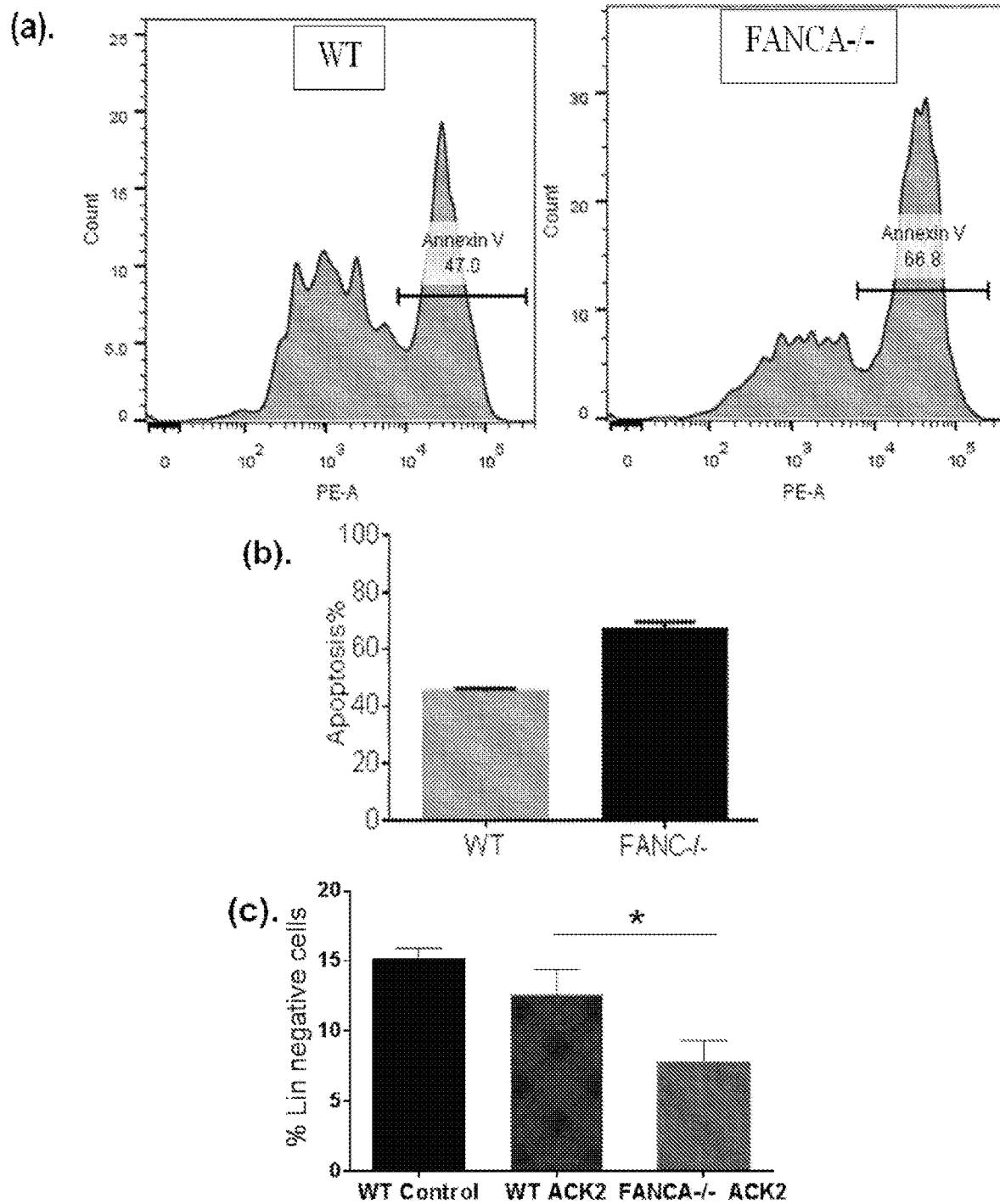
FIG. 8 shows that KIT blockade which resulted in higher apoptosis in FAN$^{-/-}$ HSPC and in-vivo KIT blockade resulted in more sustained bone marrow suppression than WT. Panel a shows percent of sorted LSK from WT and FANCA$^{-/-}$ mice cultured in SCF+TPO+ACK2 containing media. Apoptosis were measured at 72 hours. Panel b shows percent apoptotic cells in WT and FANCA$^{-/-}$ cells. Panel c shows percent lineage negative cells 7 days post ACK2 treatment.

Next, it was directly determined whether sorted FA$^{-/-}$ LSK cells showed increased sensitivity to KIT-Ab mediated apoptosis. FA$^{-/-}$ HSPC showed significantly lower proliferative potential when cultured in SCF and thrombopoietin, which was diminished even more upon addition of the KIT-Ab (FIG. 2, panel a; and FIG. 5, panels a and b). In addition, seven days following a blocking KIT antibody (e.g., ACK2) injection in vivo, evaluation of bone marrow revealed significant decrease in Lin-cells in FA$^{-/-}$ mice when compared to WT mice (FIG. 2, panel b and FIG. 6, panel a). In addition, colony forming cell units (CFU) from both femurs showed a marked reduction in FA$^{-/-}$ mice when compared to WT mice (FIG. 2, panel c). Similar results were seen in FancD2 (FD$^{-/-}$) mice (FIG. 6, panel b).

Since KIT blockade resulted in increased HSPC depletion both ex-vivo and in-vivo, it was determined whether KIT blockade alone would suffice as a HSCT conditioning regimen in FA$^{-/-}$ and FD$^{-/-}$ mice. BM transplant one week following a blocking KIT antibody (e.g., ACK2)-based conditioning resulted in mean donor chimerism of 24% at 16 weeks (FIG. 2, panel d). Evaluation of different hematopoietic compartments showed a progressive increase in donor chimerism from the HSCs to hematopoietic progenitor cells (HPCs) and differentiated blood cells, indicating increasing loss of FA hematopoietic cells during proliferation and differentiation that confers a selective advantage to the WT counterparts (FIG. 2, panel e). Stable donor HSC or the long-term repopulating cell engraftment following KIT-Ab based conditioning was also assessed in secondary transplant experiments (FIG. 2, panel f). Furthermore, donor chimerism progressively increased over the 4 month post-HSCT period, indicating that replicative stress conferred a survival advantage to WT cells (FIG. 2, panel g). Similar results were seen in FD$^{-/-}$ mice (FIG. 6, panel c).

Figure 9:
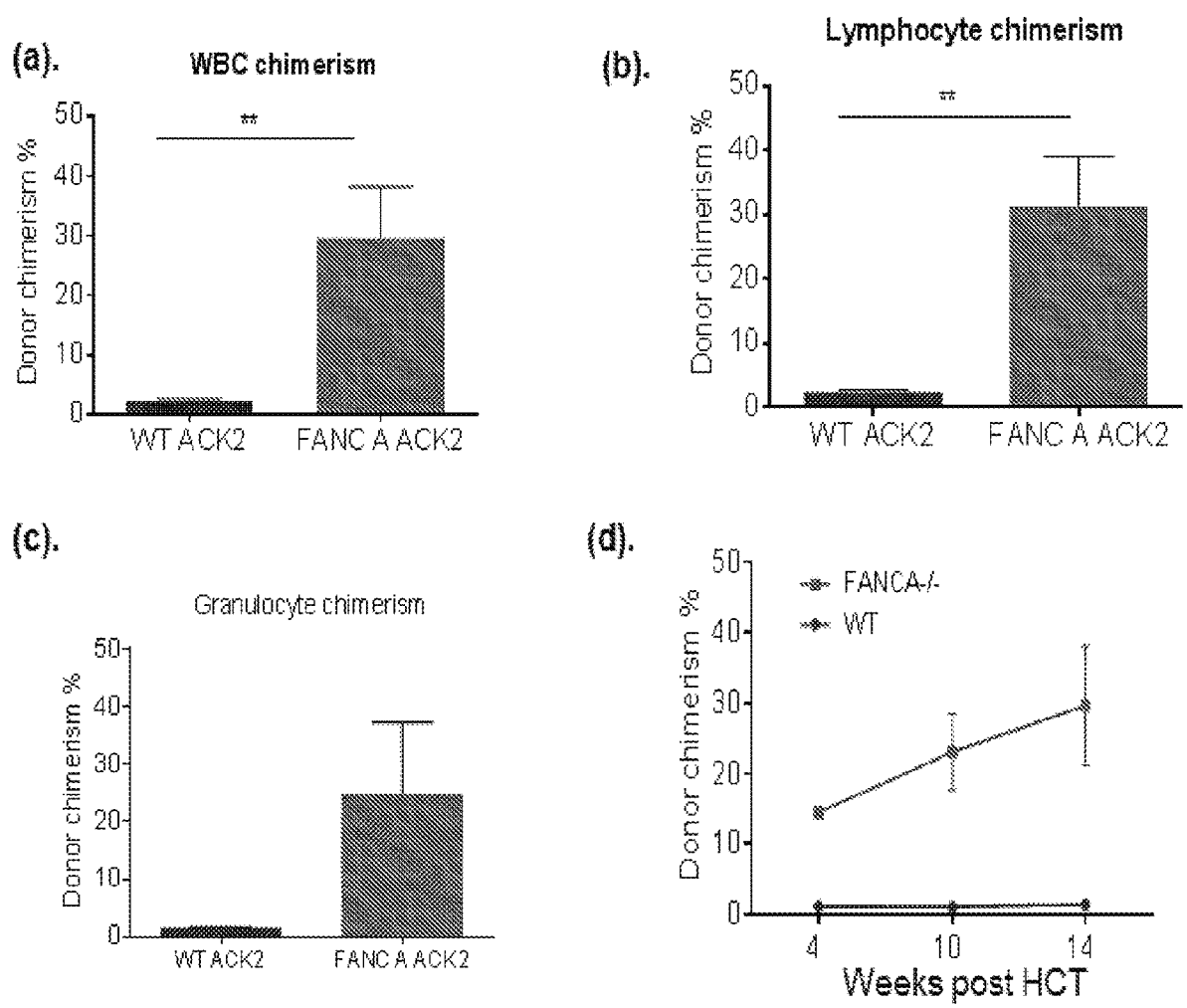
FIG. 9 shows KIT blockade based conditioning which resulted in higher donor chimerism when compared to WT mice. Donor chimerism following blocking KIT antibody (e.g., ACK2)-conditioned whole BM HSC transplantation in WBC (Panel a), lymphocyte (Panel b), and granulocytes (Panel c). Panel d is a graph showing WBC chimerism trend post HSC transplantation.

KIT blockade based conditioning which resulted in higher donor chimerism when compared to WT mice is shown in FIG. 9, panels a to d. FIG. 9, panel a shows donor chimerism following ACK2 conditioned whole BM HCT in WBC. FIG. 9, panel b shows donor chimerism following ACK2 conditioned whole BM HCT in lymphocyte. FIG. 9, panel c shows donor chimerism following ACK2 conditioned whole BM HCT in granulocytes. FIG. 9, panel d is a graph showing WBC chimerism trend post HCT.

Figure 10:
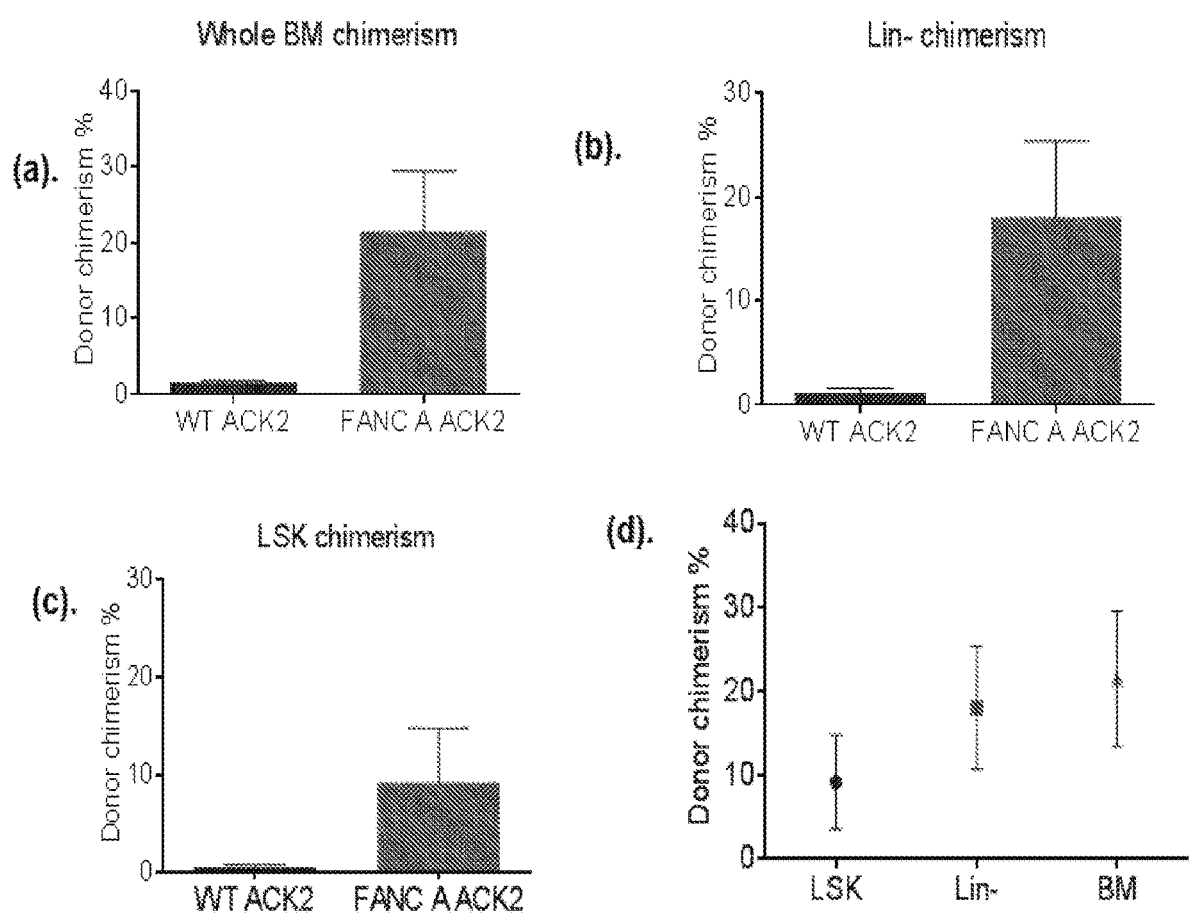
FIG. 10 shows robust donor graft seen in HSPC compartment in FANCA$^{-/-}$ mice. Donor chimerism in different bone marrow compartments, whole BM (Panel a), Lineage negative (Panel b), and LSK compartment (panel c). Panel d is a graph showing donor chimerism in different BM compartments in FANCA$^{-/-}$ mice.

Robust donor graft was seen in HSPC compartment in FANCA$^{-/-}$ mice as shown in FIG. 10, panels a to d. Donor chimerism was seen in different bone marrow compartments: FIG. 10, panel a shows whole BM; FIG. 10, panel b shows Lineage negative; and FIG. 10, panel c shows LSK compartment. FIG. 10, panel d shows is a graph showing donor chimerism in different BM compartments in FANCA$^{-/-}$ mice.

Injection of alum has been previously established to result in inflammatory stress in FancC mice. Hu et al. *The Journal of clinical investigation.* 2013; 123(9):3952-66. The stably engrafted FA$^{-/-}$ and FD$^{-/-}$ mice were therefore subjected to three monthly alum injections. FA$^{-/-}$/FD$^{-/-}$ mice chimeric for WT BM following KIT-Ab conditioning and Alum administration did not develop overt signs of bone marrow failure (BMF); notably, there was a progressive increase in WT donor chimerism in both FA$^{-/-}$ and FD$^{-/-}$ mice (FIG. 2, panel g and FIG. 6, panel c) that reached an average of 34%, with some mice with 48-49% WT engraftment within three months.

Collectively, it is presented herein that in the presence of a DNA repair defect in FA, KIT blockade can suffice as a relatively non-toxic conditioning regimen for engraftment of donor HSC. Increased sensitivity to KIT Ab mediated apoptosis has not been previously reported in FA. Herein, it is shown that FA HSPC are predisposed to KIT-Ab mediated apoptosis because the intrinsic DNA repair defect results in baseline activation of apoptosis, inflammatory and senescence pathways, resulting in increased cycling HSPC with increased KIT signaling. This discovery led to develop a KIT-Ab based HSCT conditioning regimen, which achieved nearly 25% stable engraftment in FA mice, and which further increased by 1.5 times on average with Alum-induced inflammatory stress. The findings presented herein also showed a distinct survival advantage of WT HSC. Furthermore, the level of HSC engraftment observed in vivo is clinically translatable, especially since previous reports have suggested that even a single HSC revertant in FA patients can eventually repopulate the entire bone marrow and prevent the evolution of BMF. Gross et al. *Cytogenetic and genome research.* 2002; 98(2-3):126-35; and Mankad et al. *Blood.* 2006; 107(8):3084-90. Genetically corrected FA HSC or WT HSC have been reported to have a survival advantage in FA mice under various stress conditions. Li et al. *Blood.* 2004; 104(4):1204-9; and Habi et al. *Anemia.* 2010; 2010 Article ID 947816. Hence normal physiological stressors may increase normal donor engraftment with time.

Currently, despite reduced intensity alkylator conditioning, the morbidity and further increased susceptibility to malignancy is concerning. MacMillan et al. *Blood.* 2015; 125(24):3798-804; Peffault de Latour et al. *Blood.* 2013; 122(26):4279-86; and Guardiola et al. *Blood.* 2004; 103(1): 73-7. Thus, KIT-Ab conditioning has immense translational potential as a FA HSPC-targeted non-toxic regimen that can obviate the short- and long-term morbidities associated with current conditioning regimens.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features. From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A method of conditioning a subject for a hematopoietic stem cell (HSC) transplantation, the method comprising:
administering an effective amount of an inhibitor of a stem cell growth factor receptor (KIT) to a subject who is in need of a HSC transplantation, wherein the subject is hypersensitive to at least one DNA damaging agent; wherein the subject is free of irradiation treatment or a conditioning regimen comprising a DNA damaging agent before the transplantation of the HSCs.

2. The method of claim 1, wherein the subject is defective in DNA repair.

3. The method of claim 1, wherein the subject has fanconi anemia.

4. The method of claim 1, wherein the inhibitor of KIT is selected from the group consisting of a protein, a nucleic acid, a small molecule, and a combination thereof.

5. The method of claim 4, wherein the inhibitor of KIT is a KIT blocking antibody.

6. The method of claim 5, wherein the KIT blocking antibody is a human antibody.

7. The method of claim 5, wherein the antibody binds KIT.

8. The method of claim 1, further comprising: transplanting a first population of HSCs to the subject after the administration of the inhibitor of KIT.

9. The method of claim 8, wherein the first population of HSCs is transplanted to the subject after the inhibitor of KIT is substantially cleared from serum of the subject.

10. The method of claim 8, wherein the first population of HSCs is transplanted to the subject at least 24 hours after the administration of the inhibitor of KIT.

11. The method of claim 8, wherein the first population of HSCs is transplanted to the subject at least 3 days after the administration of the inhibitor of KIT.

12. The method of claim 8, further comprising: transplanting a second population of HSCs to the subject after the transplantation of the first population of HSCs.

13. The method of claim 12, wherein the first population of HSCs, the second population of HSCs, or both are derived from bone marrow, peripheral blood cells, and/or umbilical cord blood.

14. The method of claim 13, wherein the first population of HSCs, the second population of HSCs, or both are allogeneic HSCs.

15. The method of claim 13, wherein the first population of HSCs, the second population of HSCs, or both are autologous HSCs.

16. The method of claim 12, wherein the first population of HSCs, the second population of HSCs, or both are cultured ex vivo prior to the transplantation.

17. The method of claim 1, wherein the subject is a human subject.

18. The method of claim 1, wherein the DNA damaging agent is an alkylating agent.

19. The method of claim 18, wherein the alkylating agent is busulfan.

20. The method of claim 1, wherein the inhibitor of KIT is administered by intravenous injection.

21. A method of conditioning a subject for a hematopoietic stem cell (HSC) transplantation, the method comprising:
   administering an effective amount of an inhibitor of a stem cell growth factor receptor (KIT) to a subject who is in need of a HSC transplantation, wherein the subject is free of irradiation treatment;
   wherein the subject is free of irradiation treatment or a conditioning regimen comprising a DNA damaging agent before the transplantation of the HSCs.

22. A method of treating fanconi anemia in a subject, the method comprising:
   administering an effective amount of an inhibitor of a stem cell growth factor receptor (KIT) to a subject who has fanconi anemia, and
   transplanting a first population of hematopoietic stem cells (HSCs) to the subject;
   wherein the subject is free of irradiation treatment or a conditioning regimen comprising a DNA damaging agent before the transplantation of the HSCs.

* * * * *

SEQUENCE LISTING

<160> NUMBER OF SEQ ID NOS: 2

<210> SEQ ID NO 1
<211> LENGTH: 976
<212> TYPE: PRT
<213> ORGANISM: Homo sapiens

<400> SEQUENCE: 1

```
Met Arg Gly Ala Arg Gly Ala Trp Asp Phe Leu Cys Val Leu Leu
1               5                   10                  15

Leu Leu Arg Val Gln Thr Gly Ser Ser Gln Pro Ser Val Ser Pro Gly
            20                  25                  30

Glu Pro Ser Pro Ser Ile His Pro Gly Lys Ser Asp Leu Ile Val
            35                  40                  45

Arg Val Gly Asp Glu Ile Arg Leu Leu Cys Thr Asp Pro Gly Phe Val
        50                  55                  60

Lys Trp Thr Phe Glu Ile Leu Asp Glu Thr Asn Glu Asn Lys Gln Asn
65                  70                  75                  80

Glu Trp Ile Thr Glu Lys Ala Glu Ala Thr Asn Thr Gly Lys Tyr Thr
                85                  90                  95

Cys Thr Asn Lys His Gly Leu Ser Asn Ser Ile Tyr Val Phe Val Arg
                100                 105                 110

Asp Pro Ala Lys Leu Phe Leu Val Asp Arg Ser Leu Tyr Gly Lys Glu
                115                 120                 125

Asp Asn Asp Thr Leu Val Arg Cys Pro Leu Thr Asp Pro Glu Val Thr
130                 135                 140

Asn Tyr Ser Leu Lys Gly Cys Gln Gly Lys Pro Leu Pro Lys Asp Leu
145                 150                 155                 160

Arg Phe Ile Pro Asp Pro Lys Ala Gly Ile Met Ile Lys Ser Val Lys
                165                 170                 175

Arg Ala Tyr His Arg Leu Cys Leu His Cys Ser Val Asp Gln Glu Gly
                180                 185                 190

Lys Ser Val Leu Ser Glu Lys Phe Ile Leu Lys Val Arg Pro Ala Phe
                195                 200                 205

Lys Ala Val Pro Val Val Ser Val Ser Lys Ala Ser Tyr Leu Leu Arg
        210                 215                 220

Glu Gly Glu Glu Phe Thr Val Thr Cys Thr Ile Lys Asp Val Ser Ser
225                 230                 235                 240

Ser Val Tyr Ser Thr Trp Lys Arg Glu Asn Ser Gln Thr Lys Leu Gln
                245                 250                 255

Glu Lys Tyr Asn Ser Trp His His Gly Asp Phe Asn Tyr Glu Arg Gln
                260                 265                 270

Ala Thr Leu Thr Ile Ser Ser Ala Arg Val Asn Asp Ser Gly Val Phe
            275                     280                 285

Met Cys Tyr Ala Asn Asn Thr Phe Gly Ser Ala Asn Val Thr Thr Thr
        290                 295                 300

Leu Glu Val Val Asp Lys Gly Phe Ile Asn Ile Phe Pro Met Ile Asn
305                 310                 315                 320

Thr Thr Val Phe Val Asn Asp Gly Glu Asn Val Asp Leu Ile Val Glu
                325                 330                 335

Tyr Glu Ala Phe Pro Lys Pro Glu His Gln Gln Trp Ile Tyr Met Asn
                340                 345                 350

Arg Thr Phe Thr Asp Lys Trp Glu Asp Tyr Pro Lys Ser Glu Asn Glu
            355                 360                 365
```

```
Ser Asn Ile Arg Tyr Val Ser Glu Leu His Leu Thr Arg Leu Lys Gly
    370                 375                 380

Thr Glu Gly Gly Thr Tyr Thr Phe Leu Val Ser Asn Ser Asp Val Asn
385                 390                 395                 400

Ala Ala Ile Ala Phe Asn Val Tyr Val Asn Thr Lys Pro Glu Ile Leu
                405                 410                 415

Thr Tyr Asp Arg Leu Val Asn Gly Met Leu Gln Cys Val Ala Ala Gly
            420                 425                 430

Phe Pro Glu Pro Thr Ile Asp Trp Tyr Phe Cys Pro Gly Thr Glu Gln
        435                 440                 445

Arg Cys Ser Ala Ser Val Leu Pro Val Asp Val Gln Thr Leu Asn Ser
450                 455                 460

Ser Gly Pro Pro Phe Gly Lys Leu Val Val Gln Ser Ser Ile Asp Ser
465                 470                 475                 480

Ser Ala Phe Lys His Asn Gly Thr Val Glu Cys Lys Ala Tyr Asn Asp
                485                 490                 495

Val Gly Lys Thr Ser Ala Tyr Phe Asn Phe Ala Phe Lys Gly Asn Asn
            500                 505                 510

Lys Glu Gln Ile His Pro His Thr Leu Phe Thr Pro Leu Leu Ile Gly
        515                 520                 525

Phe Val Ile Val Ala Gly Met Met Cys Ile Ile Val Met Ile Leu Thr
    530                 535                 540

Tyr Lys Tyr Leu Gln Lys Pro Met Tyr Glu Val Gln Trp Lys Val Val
545                 550                 555                 560

Glu Glu Ile Asn Gly Asn Asn Tyr Val Tyr Ile Asp Pro Thr Gln Leu
                565                 570                 575

Pro Tyr Asp His Lys Trp Glu Phe Pro Arg Asn Arg Leu Ser Phe Gly
            580                 585                 590

Lys Thr Leu Gly Ala Gly Ala Phe Gly Lys Val Val Glu Ala Thr Ala
        595                 600                 605

Tyr Gly Leu Ile Lys Ser Asp Ala Ala Met Thr Val Ala Val Lys Met
    610                 615                 620

Leu Lys Pro Ser Ala His Leu Thr Glu Arg Glu Ala Leu Met Ser Glu
625                 630                 635                 640

Leu Lys Val Leu Ser Tyr Leu Gly Asn His Met Asn Ile Val Asn Leu
                645                 650                 655

Leu Gly Ala Cys Thr Ile Gly Gly Pro Thr Leu Val Ile Thr Glu Tyr
            660                 665                 670

Cys Cys Tyr Gly Asp Leu Leu Asn Phe Leu Arg Arg Lys Arg Asp Ser
        675                 680                 685

Phe Ile Cys Ser Lys Gln Glu Asp His Ala Glu Ala Ala Leu Tyr Lys
    690                 695                 700

Asn Leu Leu His Ser Lys Glu Ser Ser Cys Ser Asp Ser Thr Asn Glu
705                 710                 715                 720

Tyr Met Asp Met Lys Pro Gly Val Ser Tyr Val Val Pro Thr Lys Ala
                725                 730                 735

Asp Lys Arg Arg Ser Val Arg Ile Gly Ser Tyr Ile Glu Arg Asp Val
            740                 745                 750

Thr Pro Ala Ile Met Glu Asp Asp Glu Leu Ala Leu Asp Leu Glu Asp
        755                 760                 765

Leu Leu Ser Phe Ser Tyr Gln Val Ala Lys Gly Met Ala Phe Leu Ala
    770                 775                 780

Ser Lys Asn Cys Ile His Arg Asp Leu Ala Ala Arg Asn Ile Leu Leu
```

```
              785                 790                 795                 800
        Thr His Gly Arg Ile Thr Lys Ile Cys Asp Phe Gly Leu Ala Arg Asp
                            805                 810                 815
        Ile Lys Asn Asp Ser Asn Tyr Val Lys Gly Asn Ala Arg Leu Pro
                            820                 825                 830
        Val Lys Trp Met Ala Pro Glu Ser Ile Phe Asn Cys Val Tyr Thr Phe
                            835                 840                 845
        Glu Ser Asp Val Trp Ser Tyr Gly Ile Phe Leu Trp Glu Leu Phe Ser
                    850                 855                 860
        Leu Gly Ser Ser Pro Tyr Pro Gly Met Pro Val Asp Ser Lys Phe Tyr
        865                 870                 875                 880
        Lys Met Ile Lys Glu Gly Phe Arg Met Leu Ser Pro Glu His Ala Pro
                            885                 890                 895
        Ala Glu Met Tyr Asp Ile Met Lys Thr Cys Trp Asp Ala Asp Pro Leu
                            900                 905                 910
        Lys Arg Pro Thr Phe Lys Gln Ile Val Gln Leu Ile Glu Lys Gln Ile
                            915                 920                 925
        Ser Glu Ser Thr Asn His Ile Tyr Ser Asn Leu Ala Asn Cys Ser Pro
                    930                 935                 940
        Asn Arg Gln Lys Pro Val Val Asp His Ser Val Arg Ile Asn Ser Val
        945                 950                 955                 960
        Gly Ser Thr Ala Ser Ser Ser Gln Pro Leu Leu Val His Asp Asp Val
                            965                 970                 975

<210> SEQ ID NO 2
<211> LENGTH: 972
<212> TYPE: PRT
<213> ORGANISM: Homo sapiens

<400> SEQUENCE: 2

Met Arg Gly Ala Arg Gly Ala Trp Asp Phe Leu Cys Val Leu Leu Leu
        1               5                   10                  15

Leu Leu Arg Val Gln Thr Gly Ser Ser Gln Pro Ser Val Ser Pro Gly
                        20                  25                  30

Glu Pro Ser Pro Pro Ser Ile His Pro Gly Lys Ser Asp Leu Ile Val
                    35                  40                  45

Arg Val Gly Asp Glu Ile Arg Leu Leu Cys Thr Asp Pro Gly Phe Val
                50                  55                  60

Lys Trp Thr Phe Glu Ile Leu Asp Glu Thr Asn Glu Asn Lys Gln Asn
        65              70                  75                  80

Glu Trp Ile Thr Glu Lys Ala Glu Ala Thr Asn Thr Gly Lys Tyr Thr
                        85                  90                  95

Cys Thr Asn Lys His Gly Leu Ser Asn Ser Ile Tyr Val Phe Val Arg
                        100                 105                 110

Asp Pro Ala Lys Leu Phe Leu Val Asp Arg Ser Leu Tyr Gly Lys Glu
                    115                 120                 125

Asp Asn Asp Thr Leu Val Arg Cys Pro Leu Thr Asp Pro Glu Val Thr
                    130                 135                 140

Asn Tyr Ser Leu Lys Gly Cys Gln Gly Lys Pro Leu Pro Lys Asp Leu
        145                 150                 155                 160

Arg Phe Ile Pro Asp Pro Lys Ala Gly Ile Met Ile Lys Ser Val Lys
                            165                 170                 175

Arg Ala Tyr His Arg Leu Cys Leu His Cys Ser Val Asp Gln Glu Gly
                            180                 185                 190
```

-continued

```
Lys Ser Val Leu Ser Glu Lys Phe Ile Leu Lys Val Arg Pro Ala Phe
            195                 200                 205
Lys Ala Val Pro Val Ser Val Ser Lys Ala Ser Tyr Leu Leu Arg
        210                 215                 220
Glu Gly Glu Glu Phe Thr Val Thr Cys Thr Ile Lys Asp Val Ser Ser
225                 230                 235                 240
Ser Val Tyr Ser Thr Trp Lys Arg Glu Asn Ser Gln Thr Lys Leu Gln
                245                 250                 255
Glu Lys Tyr Asn Ser Trp His His Gly Asp Phe Asn Tyr Glu Arg Gln
            260                 265                 270
Ala Thr Leu Thr Ile Ser Ser Ala Arg Val Asn Asp Ser Gly Val Phe
        275                 280                 285
Met Cys Tyr Ala Asn Asn Thr Phe Gly Ser Ala Asn Val Thr Thr Thr
    290                 295                 300
Leu Glu Val Val Asp Lys Gly Phe Ile Asn Ile Phe Pro Met Ile Asn
305                 310                 315                 320
Thr Thr Val Phe Val Asn Asp Gly Glu Asn Val Asp Leu Ile Val Glu
                325                 330                 335
Tyr Glu Ala Phe Pro Lys Pro Glu His Gln Gln Trp Ile Tyr Met Asn
            340                 345                 350
Arg Thr Phe Thr Asp Lys Trp Glu Asp Tyr Pro Lys Ser Glu Asn Glu
        355                 360                 365
Ser Asn Ile Arg Tyr Val Ser Glu Leu His Leu Thr Arg Leu Lys Gly
    370                 375                 380
Thr Glu Gly Gly Thr Tyr Thr Phe Leu Val Ser Asn Ser Asp Val Asn
385                 390                 395                 400
Ala Ala Ile Ala Phe Asn Val Tyr Val Asn Thr Lys Pro Glu Ile Leu
                405                 410                 415
Thr Tyr Asp Arg Leu Val Asn Gly Met Leu Gln Cys Val Ala Ala Gly
            420                 425                 430
Phe Pro Glu Pro Thr Ile Asp Trp Tyr Phe Cys Pro Gly Thr Glu Gln
        435                 440                 445
Arg Cys Ser Ala Ser Val Leu Pro Val Asp Val Gln Thr Leu Asn Ser
    450                 455                 460
Ser Gly Pro Pro Phe Gly Lys Leu Val Val Gln Ser Ser Ile Asp Ser
465                 470                 475                 480
Ser Ala Phe Lys His Asn Gly Thr Val Glu Cys Lys Ala Tyr Asn Asp
                485                 490                 495
Val Gly Lys Thr Ser Ala Tyr Phe Asn Phe Ala Phe Lys Glu Gln Ile
            500                 505                 510
His Pro His Thr Leu Phe Thr Pro Leu Leu Ile Gly Phe Val Ile Val
        515                 520                 525
Ala Gly Met Met Cys Ile Ile Val Met Ile Leu Thr Tyr Lys Tyr Leu
    530                 535                 540
Gln Lys Pro Met Tyr Glu Val Gln Trp Lys Val Val Glu Glu Ile Asn
545                 550                 555                 560
Gly Asn Asn Tyr Val Tyr Ile Asp Pro Thr Gln Leu Pro Tyr Asp His
                565                 570                 575
Lys Trp Glu Phe Pro Arg Asn Arg Leu Ser Phe Gly Lys Thr Leu Gly
            580                 585                 590
Ala Gly Ala Phe Gly Lys Val Val Glu Ala Thr Ala Tyr Gly Leu Ile
        595                 600                 605
Lys Ser Asp Ala Ala Met Thr Val Ala Val Lys Met Leu Lys Pro Ser
```

-continued

```
            610                 615                 620
Ala His Leu Thr Glu Arg Glu Ala Leu Met Ser Glu Leu Lys Val Leu
625                 630                 635                 640

Ser Tyr Leu Gly Asn His Met Asn Ile Val Asn Leu Leu Gly Ala Cys
                645                 650                 655

Thr Ile Gly Gly Pro Thr Leu Val Ile Thr Glu Tyr Cys Cys Tyr Gly
                660                 665                 670

Asp Leu Leu Asn Phe Leu Arg Arg Lys Arg Asp Ser Phe Ile Cys Ser
                675                 680                 685

Lys Gln Glu Asp His Ala Glu Ala Ala Leu Tyr Lys Asn Leu Leu His
            690                 695                 700

Ser Lys Glu Ser Ser Cys Ser Asp Ser Thr Asn Glu Tyr Met Asp Met
705                 710                 715                 720

Lys Pro Gly Val Ser Tyr Val Val Pro Thr Lys Ala Asp Lys Arg Arg
                725                 730                 735

Ser Val Arg Ile Gly Ser Tyr Ile Glu Arg Asp Val Thr Pro Ala Ile
                740                 745                 750

Met Glu Asp Asp Glu Leu Ala Leu Asp Leu Glu Asp Leu Leu Ser Phe
            755                 760                 765

Ser Tyr Gln Val Ala Lys Gly Met Ala Phe Leu Ala Ser Lys Asn Cys
            770                 775                 780

Ile His Arg Asp Leu Ala Ala Arg Asn Ile Leu Leu Thr His Gly Arg
785                 790                 795                 800

Ile Thr Lys Ile Cys Asp Phe Gly Leu Ala Arg Asp Ile Lys Asn Asp
                805                 810                 815

Ser Asn Tyr Val Val Lys Gly Asn Ala Arg Leu Pro Val Lys Trp Met
                820                 825                 830

Ala Pro Glu Ser Ile Phe Asn Cys Val Tyr Thr Phe Glu Ser Asp Val
            835                 840                 845

Trp Ser Tyr Gly Ile Phe Leu Trp Glu Leu Phe Ser Leu Gly Ser Ser
850                 855                 860

Pro Tyr Pro Gly Met Pro Val Asp Ser Lys Phe Tyr Lys Met Ile Lys
865                 870                 875                 880

Glu Gly Phe Arg Met Leu Ser Pro Glu His Ala Pro Ala Glu Met Tyr
                885                 890                 895

Asp Ile Met Lys Thr Cys Trp Asp Ala Asp Pro Leu Lys Arg Pro Thr
                900                 905                 910

Phe Lys Gln Ile Val Gln Leu Ile Glu Lys Gln Ile Ser Glu Ser Thr
            915                 920                 925

Asn His Ile Tyr Ser Asn Leu Ala Asn Cys Ser Pro Asn Arg Gln Lys
930                 935                 940

Pro Val Val Asp His Ser Val Arg Ile Asn Ser Val Gly Ser Thr Ala
945                 950                 955                 960

Ser Ser Ser Gln Pro Leu Leu Val His Asp Asp Val
                965                 970
```